United States Patent
Marmor et al.

(10) Patent No.: US 10,045,758 B2
(45) Date of Patent: Aug. 14, 2018

(54) APPARATUS, SYSTEMS AND METHODS FOR PROPER TRANSESOPHAGEAL ECHOCARDIOGRAPHY PROBE POSITIONING BY USING CAMERA FOR ULTRASOUND IMAGING

(71) Applicant: Visura Technologies, LLC, Evanston, IL (US)

(72) Inventors: David B. Marmor, Evanston, IL (US); Morgan Clyburn, Naperville, IL (US); C. Lance Boling, San Jose, CA (US)

(73) Assignee: Visura Technologies, LLC, Evanston, IL (US)

( * ) Notice: Subject to any disclaimer, the term of this patent is extended or adjusted under 35 U.S.C. 154(b) by 0 days.

(21) Appl. No.: 15/164,538

(22) Filed: May 25, 2016

(65) Prior Publication Data
US 2016/0262722 A1    Sep. 15, 2016

Related U.S. Application Data

(63) Continuation-in-part of application No. 14/952,289, filed on Nov. 25, 2015.
(Continued)

(51) Int. Cl.
*A61B 1/04* (2006.01)
*A61B 8/00* (2006.01)
(Continued)

(52) U.S. Cl.
CPC ........ *A61B 8/4254* (2013.01); *A61B 1/00103* (2013.01); *A61B 1/053* (2013.01);
(Continued)

(58) Field of Classification Search
CPC ....... A61B 5/687; A61M 25/01; A61M 39/10; A61M 2039/1027
(Continued)

(56) References Cited

U.S. PATENT DOCUMENTS 1,761,761 A * 6/1930 Vicente .................. A61B 17/24
606/108
3,877,429 A * 4/1975 Rasumoff ......... A61M 25/0668
604/158
(Continued)

FOREIGN PATENT DOCUMENTS

| WO | WO 2013/008106 | 1/2013 |
|---|---|---|
| WO | WO 2014/113530 | 7/2014 |
| WO | WO 2016/086145 | 6/2016 |

OTHER PUBLICATIONS

International Search Report and Written Opinion for PCT/US15/62701, dated Feb. 18, 2016.
(Continued)

*Primary Examiner* — Timothy J Neal
*Assistant Examiner* — Jae Woo
(74) *Attorney, Agent, or Firm* — Cooley LLP

(57) ABSTRACT

In some embodiments, a method includes releasably attaching an image capture assembly to a distal portion of a TEE device. Next, the TEE device coupled to the image capture assembly is inserted into an oral cavity of the patient. With the image capture assembly releasably attached to the distal portion of the TEE device, image data of an esophagus of the patient captured by the image capture assembly is displayed. While viewing the display of image data, the TEE device coupled to the image capture assembly can be moved within the esophagus. With both the TEE device and the image capture assembly disposed within the esophagus, the image capture assembly is detached from the TEE device. With the image capture assembly detached from the TEE device, and with the TEE device disposed at least in part within the esophagus, the image capture assembly is removed from the patient.

26 Claims, 21 Drawing Sheets

Related U.S. Application Data

(60) Provisional application No. 62/084,969, filed on Nov. 26, 2014.

(51) Int. Cl.

| | | |
|---|---|---|
| *A61B 8/08* | (2006.01) | |
| *A61B 8/12* | (2006.01) | |
| *A61B 1/05* | (2006.01) | |
| *A61B 1/06* | (2006.01) | |
| *A61B 1/273* | (2006.01) | |
| *A61B 1/00* | (2006.01) | |

(52) U.S. Cl.
CPC .......... *A61B 1/0676* (2013.01); *A61B 1/0684* (2013.01); *A61B 1/2733* (2013.01); *A61B 8/0883* (2013.01); *A61B 8/12* (2013.01); *A61B 8/4416* (2013.01); *A61B 1/00016* (2013.01); *A61B 1/00018* (2013.01); *A61B 8/445* (2013.01); *A61B 8/4483* (2013.01); *A61B 8/463* (2013.01); *A61B 8/5207* (2013.01)

(58) Field of Classification Search
USPC .......... 600/104, 109, 112, 114, 175; 606/108
See application file for complete search history.

(56) References Cited

U.S. PATENT DOCUMENTS

| | | | | |
|---|---|---|---|---|
| 4,211,234 A * | 7/1980 | Fisher | A61M 25/01 | 128/200.26 |
| 4,327,738 A | 5/1982 | Green et al. | | |
| 4,567,882 A | 2/1986 | Heller | | |
| 4,723,864 A * | 2/1988 | Umeda | A61B 1/04 | 396/17 |
| 4,773,394 A * | 9/1988 | Reichstein | A61B 1/00154 | 600/114 |
| 4,815,470 A * | 3/1989 | Curtis | A61B 8/12 | 600/459 |
| 5,251,025 A | 10/1993 | Cooper et al. | | |
| 5,390,661 A * | 2/1995 | Griffith | A61B 1/00154 | 600/114 |
| 5,400,771 A * | 3/1995 | Pirak | A61B 1/042 | 128/200.26 |
| 5,598,846 A * | 2/1997 | Peszynski | A61B 5/6826 | 600/444 |
| 5,630,782 A * | 5/1997 | Adair | A61B 1/00073 | 600/123 |
| 5,682,199 A * | 10/1997 | Lankford | A61B 1/00105 | 348/65 |
| 5,735,792 A | 4/1998 | Vanden Hoek et al. | | |
| 5,743,731 A | 4/1998 | Lares et al. | | |
| 5,846,182 A * | 12/1998 | Wolcott | A61B 1/00135 | 128/207.14 |
| 5,906,578 A * | 5/1999 | Rajan | A61B 1/00009 | 600/424 |
| 5,941,818 A * | 8/1999 | Hori | A61B 1/00073 | 600/110 |
| 5,976,075 A * | 11/1999 | Beane | A61B 1/00147 | 600/106 |
| 6,083,151 A * | 7/2000 | Renner | A61B 1/00135 | 600/112 |
| 6,156,006 A | 12/2000 | Brosens et al. | | |
| 6,162,170 A * | 12/2000 | Foley | A61B 17/3421 | 600/114 |
| 6,211,904 B1 | 8/2001 | Adair et al. | | |
| 6,275,255 B1 | 8/2001 | Adair et al. | | |
| 6,520,907 B1 * | 2/2003 | Foley | A61B 17/02 | 600/114 |
| 6,527,704 B1 * | 3/2003 | Chang | A61B 1/042 | 600/112 |
| 6,540,668 B1 * | 4/2003 | Schulz | G02B 23/2484 | 600/112 |
| 6,543,447 B2 * | 4/2003 | Pacey | A61B 1/05 | 128/200.26 |
| 6,863,674 B2 * | 3/2005 | Kasahara | A61B 17/3421 | 600/114 |
| 6,884,220 B2 | 4/2005 | Aviv et al. | | |
| 7,670,282 B2 * | 3/2010 | Mathis | A61B 1/0014 | 600/101 |
| 7,814,912 B2 * | 10/2010 | George | A61B 17/12022 | 128/200.24 |
| 7,819,817 B2 * | 10/2010 | Rahn | A61B 5/01 | 600/549 |
| 7,927,272 B2 * | 4/2011 | Bayer | A61B 1/00154 | 600/107 |
| 7,946,981 B1 * | 5/2011 | Cubb | A61B 1/00052 | 600/120 |
| 7,955,255 B2 | 6/2011 | Boulais et al. | | |
| 8,172,758 B2 | 5/2012 | Harhen | | |
| 8,360,064 B2 * | 1/2013 | Swann | A61B 17/42 | 128/830 |
| 8,416,291 B2 * | 4/2013 | Carrey | A61B 1/00039 | 348/77 |
| 8,545,396 B2 | 10/2013 | Cover et al. | | |
| 8,667,966 B2 * | 3/2014 | Koike | A61B 1/00165 | 128/200.24 |
| 8,771,173 B2 | 7/2014 | Fonger et al. | | |
| 8,882,682 B2 * | 11/2014 | Qiu | A61B 5/0084 | 128/200.26 |
| 8,926,503 B2 | 1/2015 | St. George et al. | | |
| 8,961,398 B2 * | 2/2015 | Makower | A61B 1/00135 | 600/103 |
| 9,560,954 B2 * | 2/2017 | Jacobs | A61B 1/00112 | |
| 2002/0082477 A1 * | 6/2002 | Kim | A61B 1/00142 | 600/186 |
| 2002/0198583 A1 * | 12/2002 | Rock | A61N 1/0517 | 607/122 |
| 2003/0036681 A1 * | 2/2003 | Aviv | A61B 1/2733 | 600/129 |
| 2003/0120168 A1 | 6/2003 | Atlee, III | | |
| 2003/0208107 A1 * | 11/2003 | Refael | A61B 1/0008 | 600/300 |
| 2004/0102804 A1 | 5/2004 | Chin | | |
| 2004/0210105 A1 * | 10/2004 | Hale | A61B 1/00183 | 600/101 |
| 2004/0215058 A1 * | 10/2004 | Zirps | A61B 1/0008 | 600/127 |
| 2005/0090712 A1 * | 4/2005 | Cubb | A61B 1/00073 | 600/120 |
| 2005/0119523 A1 * | 6/2005 | Starksen | A61B 17/00234 | 600/109 |
| 2005/0273012 A1 | 12/2005 | Aviv et al. | | |
| 2006/0149129 A1 | 7/2006 | Watts et al. | | |
| 2006/0241476 A1 * | 10/2006 | Loubser | A61B 8/4209 | 600/463 |
| 2006/0276693 A1 | 12/2006 | Pacey | | |
| 2006/0281971 A1 * | 12/2006 | Sauer | A61B 34/20 | 600/109 |
| 2007/0083225 A1 * | 4/2007 | Kiser | A61B 17/29 | 606/192 |
| 2007/0135803 A1 * | 6/2007 | Belson | A61B 1/00154 | 606/1 |
| 2007/0137651 A1 * | 6/2007 | Glassenberg | A61M 16/04 | 128/207.15 |
| 2007/0175482 A1 * | 8/2007 | Kimmel | A61B 1/018 | 128/207.14 |
| 2007/0203517 A1 | 8/2007 | Williams et al. | | |
| 2008/0255441 A1 * | 10/2008 | Hadani | A61B 1/00105 | 600/373 |
| 2008/0312507 A1 * | 12/2008 | Kim | A61B 1/00052 | 600/188 |
| 2008/0319350 A1 * | 12/2008 | Wallace | A61B 5/053 | 600/587 |
| 2011/0178372 A1 | 7/2011 | Pacey et al. | | |
| 2011/0263983 A1 * | 10/2011 | Peszynski | A61B 1/0052 | 600/443 |
| 2013/0150710 A1 * | 6/2013 | Zentgraf | A61B 8/461 | 600/424 |

(56) References Cited

U.S. PATENT DOCUMENTS

| | | | |
|---|---|---|---|
| 2013/0184571 A1* | 7/2013 | Wilkening | A61B 90/39 |
| | | | 600/426 |
| 2013/0317300 A1* | 11/2013 | Berci | A61B 1/0005 |
| | | | 600/188 |
| 2014/0018668 A1 | 1/2014 | Zheng et al. | |
| 2014/0081080 A1 | 3/2014 | Intoccia et al. | |
| 2015/0320392 A1* | 11/2015 | Missov | A61B 90/50 |
| | | | 600/466 |
| 2016/0150947 A1* | 6/2016 | Marmor | A61B 1/00045 |
| | | | 600/110 |
| 2017/0258440 A1 | 9/2017 | Marmor | |
| 2018/0092625 A1 | 4/2018 | Marmor et al. | |

OTHER PUBLICATIONS

Extended European Search Report for European Application No. 15862735.6, dated Apr. 26, 2018, 10 pages.

Office Action for U.S. Appl. No. 15/834,878, dated Feb. 9, 2018, 17 pages.

\* cited by examiner

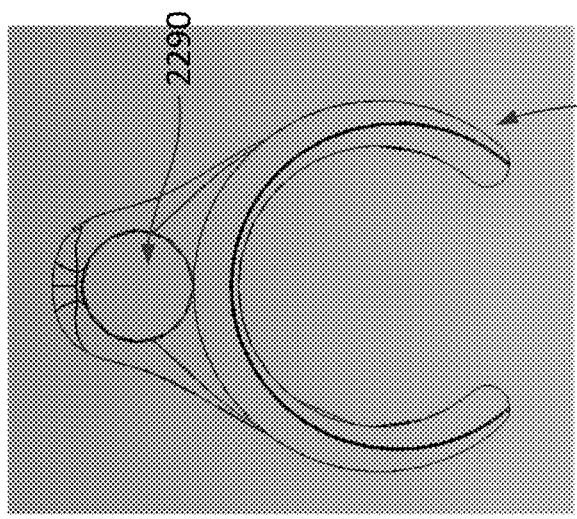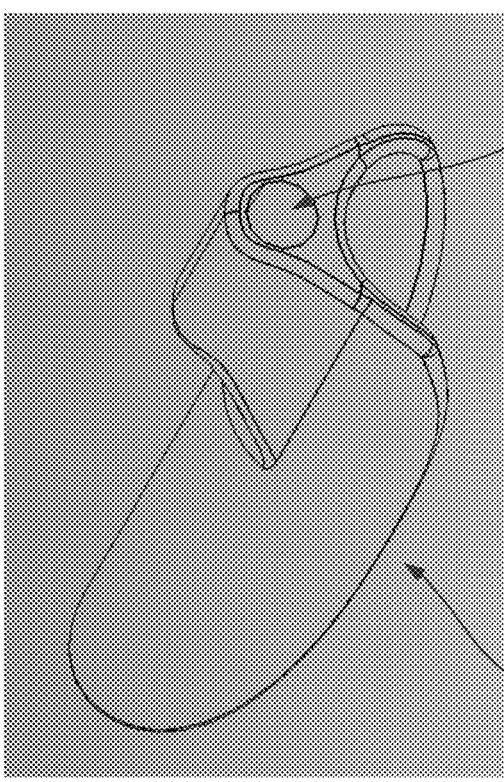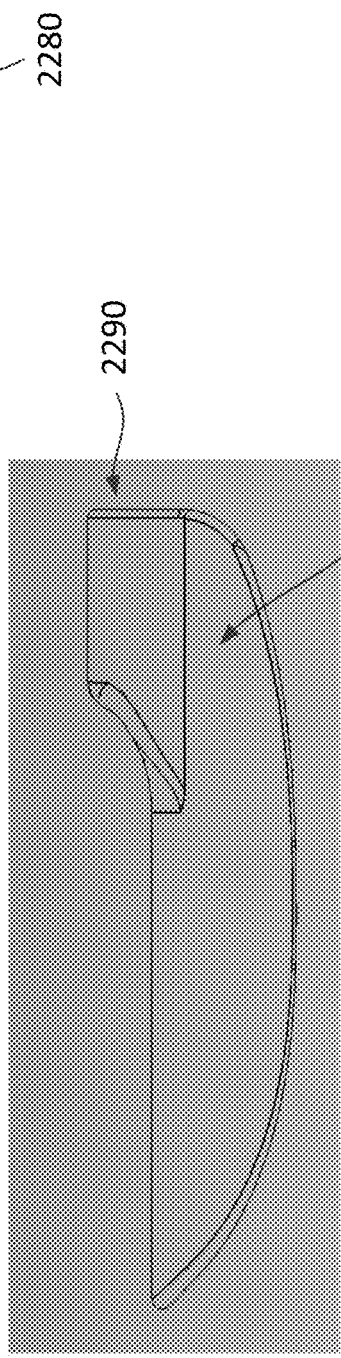

APPARATUS, SYSTEMS AND METHODS FOR PROPER TRANSESOPHAGEAL ECHOCARDIOGRAPHY PROBE POSITIONING BY USING CAMERA FOR ULTRASOUND IMAGING

CROSS-REFERENCE TO RELATED APPLICATIONS

This application is a continuation-in-part of U.S. patent application Ser. No. 14/952,289, filed Nov. 25, 2015, which claims priority to and the benefit of U.S. Provisional Application No. 62/084,969, filed Nov. 26, 2014, the contents of each of which are incorporated by reference herein in their entirety.

BACKGROUND

The embodiments described herein relate generally to the field of transesophageal echocardiography (TEE) and more particularly to apparatus, systems, and methods for assisting TEE intubation.

Echocardiography is a common diagnostic procedure that utilizes a transducer to transmit ultrasound waves to, for example, a heart, which deflect or rebound off the structures of the heart. A computer converts the resulting waves and displays them on a screen to allow an operator (e.g., a cardiologist) to assess cardiac structure and function. Some known echocardiograms are obtained from a transthoracic echocardiography (TTE) approach. Echocardiograms obtained from the TTE approach, however, are limited to capturing images through the patient's chest wall. Other known echocardiograms are obtained from a transesophageal echocardiography (TEE) approach. A TEE approach, similar to the TTE approach, allows for capturing of images of the heart, however, the images can be captured from the esophagus rather than through the chest wall. As such, the TEE approach can provide optimal imaging (e.g., clearer images), for example, of heart valves, assessing for left atrial appendage thrombus, examination of intracardiac tumors, assessment for intracardiac shunting, etc., when compared to the TTE approach.

Known TEE probes include a flexible endoscope with an ultrasound transducer at its tip. During the TEE procedure, the probe is inserted into a patient's mouth and advanced into the esophagus. From the esophageal position, the ultrasound beam does not have to travel through the chest wall (as compared to the TTE approach) and therefore offers a much clearer image of several key heart structures, especially the atria and valves, that may not be seen as clearly with a TTE. During the procedure, the cardiologist can rotate the endoscope and examine the heart from different angles.

Further, in known TEE procedures with known TEE devices, an operator inserts the flexible endoscope blindly, i.e., without seeing where the endoscope is moving within the patient. The procedure is typically accomplished by the operator's feel and experience. Some procedures, due in part to the blind nature of the procedure, result in catastrophic complications (e.g., oropharyngeal, esophageal, and/or gastric trauma, perforation, and/or laceration) with high mortality rates. In addition, TEE related complications result in substantial additional cost and additional days for the patient in an intensive care unit.

Thus, a need exists for improved apparatus, systems, and methods for an image capture device configured to be releasably attached to existing TEE probes for insertion into and placement of the TEE probe within a patient's esophagus, and configured to be released from the TEE probe and removed from the esophagus, leaving the transducer at the end of the TEE probe in the proper position (e.g., within the esophagus) for capturing images (e.g., of the heart). Allowing an operator to view the esophagus while placing the TEE probe therein helps to solve the problems resulting from blind intubation. Adding visualization to the TEE procedure can reduce the rate of complications because the operator can accurately use imaging to avoid misplacement of the TEE probe and trauma due in part to varying anatomy. Further, a need exists for providing such imaging capabilities to existing TEE probe models without interfering with the echocardiogram image capture, without requiring significant modifications to existing TEE probe hardware, and without adding significant size (e.g., cross-sectional area) to the TEE probe.

SUMMARY

Apparatus, systems, and methods for assisting transesophageal echocardiography (TEE) intubation are described herein. In some embodiments, devices for providing visualization in real-time of a TEE intubation are described herein. Such a device includes an image capture assembly. The image capture assembly is configured to be removably coupled to an imager head of a transesophageal echocardiography endoscopic (TEE) device, and inserted into an esophagus of a patient when removably coupled to the imager head of the TEE device. The apparatus further includes a retrieval tension member coupled to the image capture assembly. The retrieval tension member is configured to extend from the image capture assembly through the esophagus and out the patient when (1) the image capture assembly is removably coupled to the TEE device, and (2) the TEE device is disposed within a target imaging location of the esophagus.

BRIEF DESCRIPTION OF THE DRAWINGS

FIGS. 9A-9C are perspective, front, and side views, respectively, of a CAD handle of the CAD of FIG. 4.

DETAILED DESCRIPTION

Figure 1:
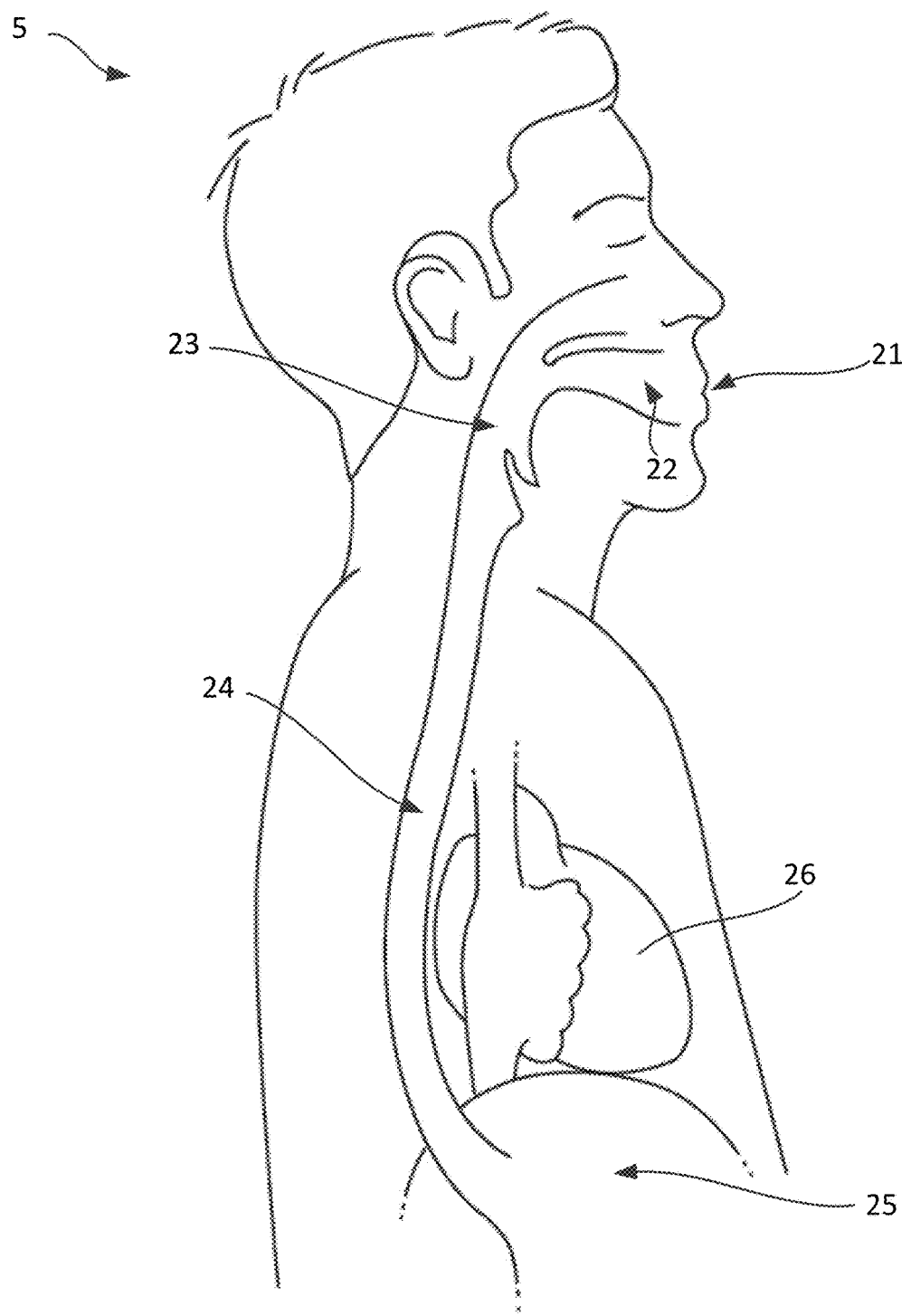
FIG. 1 is a cross-sectional view of an illustration of a portion of the human digestive system.

Apparatus, systems, and methods for assisting transesophaegeal echocardiography intubation are described herein. In some embodiments, an apparatus includes an image capture assembly. The image capture assembly is configured to be removably coupled to an imager head of a transesophageal echocardiography endoscopic (TEE) device, and inserted into an esophagus of a patient when removably coupled to the imager head of the TEE device. The apparatus further includes a retrieval tension member coupled to the image capture assembly. The retrieval tension member is configured to extend from the image capture assembly through the esophagus and out the patient when (1) the image capture assembly is removably coupled to the TEE device, and (2) the TEE device is disposed within a target imaging location of the esophagus.

In some embodiments, a method can include releasably attaching an image capture assembly to a distal portion of a TEE device. With the image capture assembly releasably attached to the distal portion of the TEE device, the TEE device coupled to the image capture assembly can be inserted into an oral cavity of the patient. With the image capture assembly releasably attached to the distal portion of the TEE device, image data of an esophagus of the patient captured by the image capture assembly can be displayed. In this manner, an operator of the device can view a real-time representation of the esophagus of the patient (e.g., to assist in TEE intubation). While viewing the display of image data, the TEE device coupled to the image capture assembly can be moved within the esophagus. With both the TEE device and the image capture assembly disposed within the esophagus, the image capture assembly can be detached from the TEE device (e.g., detached from an imager head of the TEE device). With the image capture assembly detached from the TEE device, and with the TEE device disposed at least in part within the esophagus (e.g., the TEE imager head disposed within the esophagus), the image capture assembly can be removed from the patient.

As used herein, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the words "proximal" and "distal" refer to the direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the end of a TEE device described herein first inserted inside the patient's body would be the distal end, while the opposite end of the TEE device (e.g., the end of the medical device being manipulated by the operator) would be the proximal end of the device.

The embodiments described herein can be formed or constructed of one or more biocompatible materials and/or blends thereof. Examples of suitable biocompatible materials include metals, glasses, ceramics, or polymers.

FIG. 1 is an illustration of a portion of a human digestive system, for example, to provide context to the description of the devices and methods herein. Said another way, while specific portions of the human digestive system are shown and described, it is not meant to be an exhaustive discussion of the human digestive system. Rather, pertinent anatomical structures, passageways, etc. are presented by way of example to illustrate a use of the devices and methods described herein. While the human digestive system is shown in and described with respect to FIG. 1, the devices and methods described herein can be used in other portions of a body. As shown in FIG. 1, an upper region of a patient 5 includes, inter alia, access to the digestive system via the mouth 21. The digestive system includes the mouth 21, the oral cavity 22, the pharynx 23, the esophagus 24, and the stomach 25. As shown, the mouth 5 is in fluid communication with and provides access to the oral cavity 22. Distal to and in fluid communication with the oral cavity 22 is the pharynx 23; distal to and in fluid communication with the pharynx 23 is the esophagus 24; and distal to and in fluid communication with the esophagus 24 is the stomach 25. The heart 26 is located adjacent to the esophagus 24 and above the stomach 25, as shown.

Because the esophagus 24 is located in close proximity to the heart (e.g., upper chambers of the heart), the esophagus 24 provides suitable minimally and/or noninvasive access for a transesophageal echocardiography (TEE) device to be inserted into the esophagus 24 (through the mouth 21, oral cavity 22 and pharynx 23) to capture clear, detailed, and unique images of the heart 26 (e.g., the heart chambers, valves, tumors, etc.) and/or other anatomy associated therewith (e.g., blood vessels connected to the heart), as described in further detail herein. For example, a TEE device can include a transducer at its distal end that is inserted into the esophagus 24 and is configured to send sound waves to the heart 5 and receive the echoes that bounce back from the heart 5. Such echoes can be converted to a suitable visual representation and displayed, for example, on a display device outside of the patient 5. Compared to standard echocardiograms (e.g., non-transesophageal, transthoracic), a TEE device can provide clearer images, for example, of the upper chambers of the heart 26 and the valves between the upper and lower chambers of the heart 26, thereby providing more accurate and effective diagnostic data. Further, in some instances, for example, in which a patient has an abnormally thick chest wall, is overweight, is using a ventilator, or is otherwise affected by something that minimizes the effectiveness of a standard echocardiogram, a TEE device can provide the desired images of the heart to assess the heart's structure and/or function, and diagnose any issues associated therewith. TEE devices can further be used during and/or in conjunction with other procedures, e.g., during a procedure to repair a heart valve.

As discussed in more detail herein, when passing a TEE probe through a patient's esophagus, it is desirable to minimize physical contact with portions of the esophagus and surrounding anatomy to avoid trauma thereto. In some embodiments, an apparatus (e.g., a camera assist device (CAD)) can facilitate TEE intubation by providing to the operator (e.g., a cardiologist) with images in real-time as the TEE probe is inserted into the patient and/or passed through the esophagus, and in some instances, the stomach. For example, a CAD can be removably attached to a TEE probe during insertion of the TEE probe into a patient and to a desirable position within the patient to allow an operator to visualize in real-time various anatomies (e.g., esophagus, stomach, and the like) of the patient during the intubation. In this manner, the operator can insert, maneuver, and/or dispose the TEE probe within the patient while limiting and/or preventing undesirable trauma (e.g., oropharyngeal trauma, esophageal trauma, gastric trauma, etc.) and/or related complications due in part to inserting a probe without visual cues.

Such a releasably attachable CAD can be configured to be compatible with various existing TEE probe models without interfering with the echocardiogram image capture, without requiring significant modifications to existing TEE probe hardware, and without adding significant size to the TEE probe.

Figure 2A:
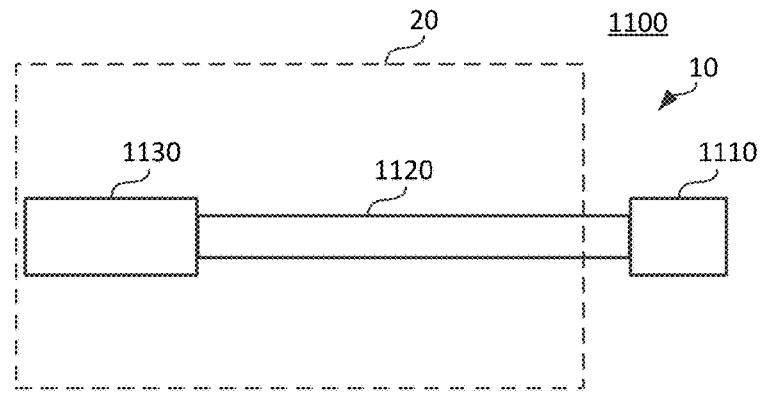
FIG. 2A is a schematic illustration of a transesophageal echocardiography endoscopic (TEE) device.
Figure 2B:
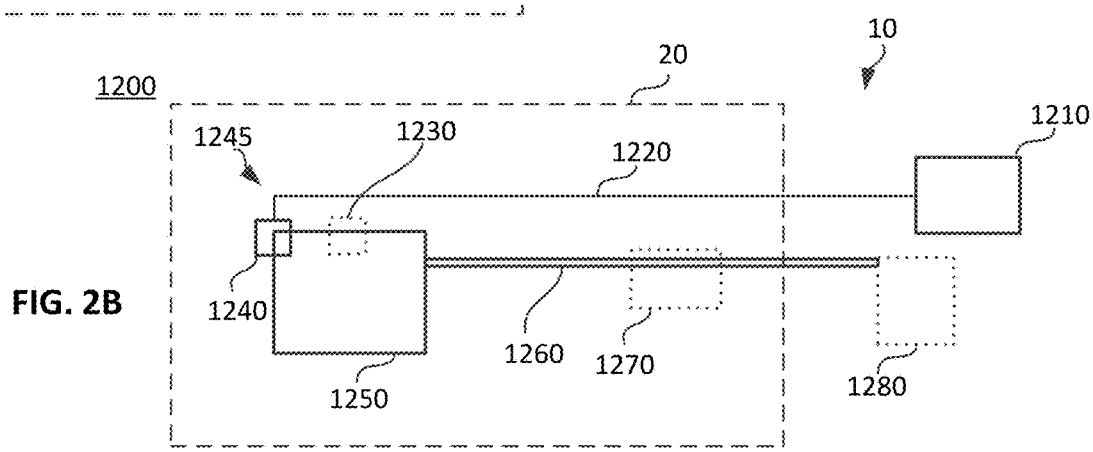
FIG. 2B is a schematic illustration of a camera assist device (CAD)
Figure 2C:
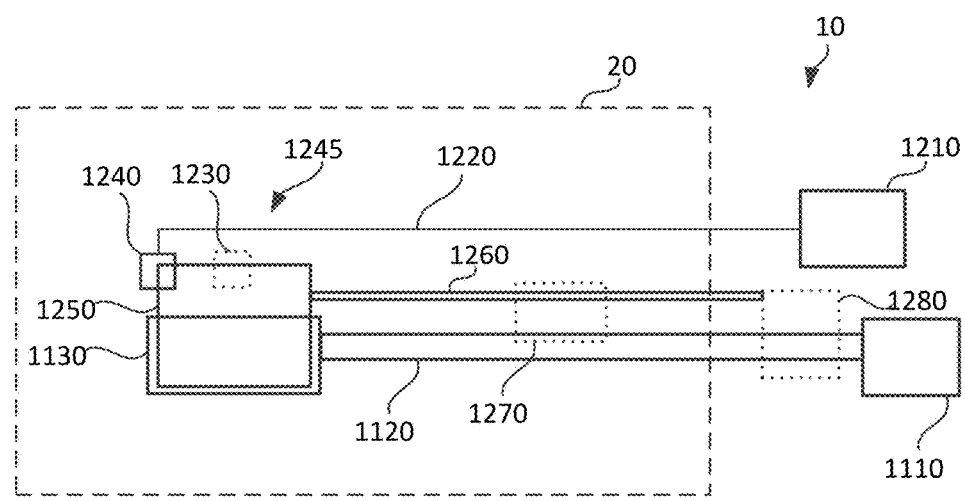
FIG. 2C is a schematic illustration of the CAD releasably attached to the TEE device, according to an embodiment.

FIG. 2C is a schematic illustration of a CAD 1200 removably attached to a TEE probe 1100 with both the CAD 1200 and the TEE probe 1100 partially disposed inside a patient, illustrated by dashed box 20, (e.g., an esophagus of the patient during a TEE intubation), according to an embodiment. FIG. 2A is a schematic illustration of the TEE probe 1100 (separated from the CAD 1200), and FIG. 2B is a schematic illustration of the CAD 1200 (separated from the TEE probe 1100). The CAD 1200 can be configured to be removably attached to any TEE probe (also referred to herein as "TEE device") suitable for TEE intubation. The TEE probe 1100 can include a TEE body 1120 having a TEE imager head 1130 coupled to its distal end and a TEE controller 1110 coupled to its, opposite, proximal end. The TEE imager head 1130 can include an ultrasound transducer (or any other suitable imaging device) configured to capture image data of, for example, a heart of the patient. For example, with the imager head 1130 disposed within the esophagus of a patient, the imager head 1130 can be configured to transmit ultrasound waves to the heart and receive waves deflecting and/or rebounding therefrom. An image processor (not shown) can transform the image data (e.g., ultrasound waves) and transmit the transformed data to a visual display (not shown) outside the patient (labeled with reference no. 10 outside the dashed box 20 to illustrate an area outside the patient). In this manner, with the TEE imager head 1130 disposed within the patient 20 (e.g., within the esophagus of the patient), an operator (e.g., a cardiologist) can view from outside the patient 10 a graphical representation of the heart and surrounding anatomy inside the patient 20.

To facilitate such insertion of the TEE imager head 1130, the CAD 1200 can be removably coupled to the TEE imager head 1130 prior to and during the insertion into and passage through the esophagus of the patient to provide the operator with real-time images of the passageway and surrounding anatomy. With access to such real-time images, the operator can limit or avoid undesirable and/or inadvertent contact with the esophagus and/or associated anatomy, thereby limiting and/or preventing complications, and in extreme circumstances, mortality. Additionally, with such access to real-time images, the operator can easily and repeatedly locate various regions of interest within the esophagus in which to dispose the TEE imager head 1130 for imaging of the heart and other anatomy. As described in more detail herein, after assistance from the CAD 1200 in moving the TEE imager head 1130 in the esophagus to a target region of the esophagus (e.g., a region in which the TEE imager head 1130 can send signals to and receive signals from target anatomy, such as the heart), the CAD 1200 can be decoupled and/or removed from the TEE imager head 1130. With the CAD 1200 decoupled from the TEE imager head 1130, the CAD 1200 can be withdrawn proximally through the esophagus 24, oral cavity 22, and out the mouth 21 of the patient, leaving the TEE imager head 1130 disposed within the target region of the esophagus 24.

As shown in FIG. 2B separated from the TEE probe, the CAD 1200 can include an image capture device 1240 configured to capture image data within a digestive system of a patient, an illumination device 1230 configured to illuminate at least a portion of the digestive system to increase quality of the image data captured by the image capture device 1240, and a coupling member 1250 configured to releasably attach to the TEE imager head 1130 of the TEE device 1100 (the illumination device 1230, image capture device 1240, and coupling member 1250 collectively referred to herein as "image capture assembly 1245"). As discussed in further detail herein, the image capture device 1240 can be configured to send the image data it captures across a communication line 1220 (see e.g., FIGS. 2B and 2C) extending from the image capture device 1240 to a graphical display device 1210. The graphical display device 1210 can be configured to display a graphical representation of the image data, thereby providing an operator of the TEE device 1100 with visual access in real-time to various portions within the digestive system of the patient.

The image capture device 1240 can be any suitable component, subsystem, device and/or combination of devices configured to capture image data (e.g., a single image and/or a series of images (a video)). The image capture device 1240 can include a sensor and a lens, and can be configured to transmit image data captured within the patient to the graphical display device 1210 disposed outside the patient via the communication line 1220. In some instances, the lens can be disposed at a distal end of the image capture assembly 1245. In this manner, the image capture device 1240 can capture image data immediately distal to and/or immediately downstream of the image capture assembly 1245. Although the sensor and lens are shown and described with respect to FIG. 2B as being collocated, in some instances, the sensor and lens can be located in any suitable portion of the image capture assembly 1245. For example, in some embodiments, the lens can be located at a distal end of the image capture assembly 1245, while the sensor can be located at a proximal end portion or a medial portion of the image capture assembly 1245.

In some instances, the image capture device 1240 can include an image processor (not shown) configured to process the image data such that the image data can be graphically displayed on the graphical display device 1210. In other instances, for example, to allow for a smaller form factor of the image capture device 1240, processing of the image data can occur entirely outside the patient and distinct from the image capture device 1240. In such instances, the image data can be processed, for example, at an image processor of the graphical display device 1210. In yet further instances, the image data can be processed at an image processor separate from both the graphical display device 1210 and the image capture device 1240, and the sent to the graphical display device 1210 to be displayed. In some instances, the image capture device 1240 can include wireless capabilities. For example, in such instances, the image capture device 1240 can communicate wirelessly with an image processor and/or the graphical display device 1210. In this manner, image data can be transmitted from the image capture device 1240 when disposed within the patient to outside the patient without any physical wires.

To enhance the quality of image data captured by the image capture device 1240, the CAD 1200 can optionally include an illumination device 1230 (as shown in dotted form in FIGS. 2B and 2C). The illumination device 1230 can be configured to illuminate a target area (e.g., within the esophagus) in which the image capture device 1240 can capture image data. The illumination device 1230 can include any suitable illumination source or interface. For example, in some instances, an illumination device 1230 can include a light emitting diode (LED). In some instances, the illumination device 1230 can be separate from the image capture device 1240, while in other instances, the illumination device 1230 can be collocated with and/or integral to the image capture device 1240. In some instances, for example, in which the image capture device 1240 includes an infrared sensor, the CAD 1200 may exclude an illumination device 1230.

In some instances, the communication line 1220 can include one or more optical fibers. In such instances, light can be received at the image capture device 1240, transmitted via the optical fiber(s) of the communication line 1220, and converted outside the patient to an electronic signal. In this manner, with the image processing taking place entirely outside the patient during the TEE intubation, the image capture assembly 1245 can have a smaller form factor. In such instances, the illumination device 1230 can include one or more LEDs. Further, in some instances, the optical fiber can be disposed of after the procedure, while other components of the CAD 1200 can sterilized and reused in subsequent procedures.

In some instances, one or both of the image capture device 1240 and the illumination device 1230 can be controlled remotely via the communication line 1220. For example, in such instances, the image capture device 1240 can receive via the communication line 1220 a signal including instructions to capture one or more images, and/or the illumination device 1230 can receive power and/or a signal to illuminate. In some instances, one or both of the image capture device 1240 and the illumination device 1230 can receive power via the communication line 1220 from a power source external to patient. In other instances, one or both of the image capture device 1240 and the illumination device 1230 can include a power source (e.g., a battery) configured to store power sufficient for operation of one or both of the image capture device 1240 and the illumination device 1230.

In some instances, the image capture device 1240 can include a lens filter (e.g., ultraviolet filter, infrared filter, etc.) (not shown). An image filter can provide an operator of the CAD 1200 visual indicators within the patient's digestive system. For example, in some instances, when moving the CAD 1200 within the patient, an operator may want to avoid certain weak portions (or portions otherwise particularly susceptible to damage and/or trauma) of the digestive system (e.g., esophagus). In such instances, a lens filter can provide visual indicators to the operator when a graphical representation of the image data is displayed.

To facilitate insertion of the CAD 1200 removably coupled to the TEE device 1100 into the patient and through the esophagus, and similarly, withdrawal of the CAD 1200 from the patient when the CAD 1200 is detached from the TEE device 1100, the image capture assembly 1245 can be configured to change between a first configuration, in which the image capture assembly 1245 has a first cross-sectional area, to a second configuration, in which the image capture assembly 1245 has a second cross-sectional area smaller than the first cross-sectional area. In this manner, the image capture assembly 1245 can be disposed in its first, larger configuration when the operator desires to view images captured by the image capture device 1240, and the image capture assembly 1245 can be transitioned to its second, smaller configuration, when the operator desires to move the image capture assembly 1245 through one or more relatively narrow portions of the patient (e.g., narrow portions of the esophagus). For example, an operator can transition the image capture assembly 1245 between configurations to avoid portions of the patient (e.g., the esophagus) that are particularly susceptible to trauma.

The CAD 1200 can further include a retrieval tension member 1260 that can be operable to decouple the image capture assembly 1245 of the CAD 1200 from the TEE imager head 1130. As shown, for example, in FIG. 1B, a distal end portion of the retrieval tension member 1250 can be coupled to the coupling member 1250 of the CAD 1200, and an opposite, proximal end portion of the retrieval tension member 1260 can be coupled to a CAD handle 1280. The CAD handle 1280 can include a holding device or member that can be used to hold and/or control the retrieval tension member 1260 extending from the CAD handle 1280 during TEE intubation and removal of the CAD 1200 from the patient. The holding device or member can be configured to releasably attach to a proximal end portion of the TEE device 1100 (e.g., a proximal portion of the TEE body 1120). Further, in some instances, the CAD handle 1280 can include or be coupled to an actuator or the like that can be operable in releasing the coupling member 1250 of the CAD 1200 from the TEE imager head 1130. In this manner, in use, for example, with the TEE device 1100 (and the image capture assembly 1245 removably attached thereto) disposed within a target region of the esophagus, an operator can pull, actuate and/or otherwise manipulate the holding device or member, handle, actuator or the like of the CAD handle 1280, and in turn, pull, actuate, and/or otherwise manipulate the retrieval tension member 1250 to release the coupling member 1250 of the image capture assembly 1245 from the TEE imager head 1130 and withdraw the retrieval tension member through the digestive system and out the patient, leaving the TEE device 1100 disposed within the esophagus. In some instances, the CAD handle 1280 can be used by the operator to manipulate movement of the retrieval tension member 1260 and/or the coupling member 1250, and/or to actuate the coupling member 1250. In instances in which the image capture assembly 1245 is reconfigurable between configurations, as discussed in further detail herein, the CAD handle 1280 can be used to transition the image capture assembly 1245 between its configurations.

As shown in FIG. 2C, the image capture assembly 1245 of the CAD 1200 is configured to removably or releasably attach to the TEE imager head 1130 via the coupling member 1250. The coupling member 1250 can be configured to releasably attach to the TEE imager head 1130 in any suitable manner and can include any suitable fastening feature (e.g., mount(s), notch(es), groove(s), indent(s), slot(s), shoulder(s), adhesive(s), latch(es), magnetic coupling(s), electromagnetic coupling(,) threaded coupling(s), a friction fit, an interference fit, a snap-fit, and/or the like).

In some instances, the coupling member 1250 can include a concave portion configured to receive and/or circumscribe at least in part a portion of the TEE imager head 1130. By receiving a portion of the TEE imager head 1130 in the concave portion of the coupling member 1250, the combined cross-sectional area of the TEE imager head 1130 and the image capture assembly 1245 of the CAD 1200 can be desirably small while providing coupling retention forces sufficient to maintain coupling between the TEE imager head 1130 and the coupling member 1250 during movement of the TEE device 1100 and CAD device 1200 through the patient's digestive system. The coupling member 1250 can be configured to resist any suitable force. For example, in some instances, the coupling member 1250 can be configured to resist forces up to about 10 Newton (N). In such instances, the coupling member 1250 can be configured to release from the TEE imager head 1130 in response to a force above about 10 N (e.g., 11 N). As another example, in some instances, the coupling member 1250 can be configured to resist forces up to about 15 N. In such instances, the coupling member 1250 can be configured to release from the TEE imager head 1130 in response to a force above about 15 N (e.g., 16 N). In use, for example, an operator can apply a force (for example, via the tension member 1260) exceeding the force at which the coupling member 1250 is configured to resist when releasably attached to the TEE imager head 1130 to decouple the coupling member 1250 from the TEE imager head 1130. As discussed in more detail herein, the operator can apply the force at the CAD handle 1280.

In some instances, the coupling member 1250 can include a magnetic mechanism configured to releasably attach to the TEE imager head 1130 by magnetic force. In use, with the coupling member 1250 releasably attached to the TEE imager head 1130 by the magnetic mechanism, an operator can apply a force (e.g., pull the retrieval tension member 1260) sufficient to overcome the magnetic force of the magnetic mechanism to release the coupling member 1250 from the TEE imager head 1130.

In some instances, the coupling member 1250 can include an electromagnetic mechanism (e.g., one or more electromagnets) configured to releasably attach to the TEE imager head 1130 by electromagnetic force when energized. In such instances, the electromagnetic mechanism can be energized (e.g., receive an electric current) via the communication line 1220 by an energy source configured to be located outside the patient during the TEE intubation. The electromagnetic mechanism of the coupling member 1250, when energized, can produce a magnetic field sufficient to releasably attach to the TEE imager head 1130. In this manner, in use for example, the electromagnetic mechanism can be energized and releasably attached to the TEE imager head 1130 prior to inserting the TEE device 1100 into the patient. With the TEE device disposed in a target region (e.g., the esophagus) within the patient, the electromagnetic mechanism can be deenergized to release the coupling member 1250 from the TEE imager head 1100. An operator can control the electric current sent to the coupling member 1250. For example, in some instances, the energy source can be located at and/or controlled at the CAD handle 1280. In other instances, the energy source can be located and/or controlled at a control device (not shown) separate from the CAD handle 1280 of the CAD 1200.

In some instances, the coupling member 1250 can include a mechanical latch configured to releasably attach to the TEE imager head 1130 when the mechanical latch is disposed in its engaged configuration. The mechanical latch can be configured to transition to a disengaged position to release the coupling member 1250 from the TEE imager head 1130. The mechanical latch can be controlled remotely by the operator. For example, the mechanical latch can be operably coupled to the CAD handle 1280 via the retrieval tension member 1260. In this manner, the CAD handle 1280 can be operable to cause the mechanical latch to transition between its engaged and disengaged configurations.

In some instances, the coupling member 1250 can be formed such that it can be deformed (compressed and/or expanded) and, when released, return to its original (undeformed) shape. To achieve this, the coupling member 1250 can include or be formed from materials, such as metals or plastics, for example, that have shape memory properties. For example, in some instances, the coupling member can include or be formed from Nitinol®. In such instances, the Nitinol® can be treated (e.g., heated to a martensitic temperature, and then quenched) such that it can readily revert to its memory shape at a calibrated temperature. With such properties, the coupling member 1250, when heated (and expanded) can be disposed about the TEE imager head 1130, and then allowed to cool. When cooled, the coupling member 1250 can be sufficiently releasably coupled to the TEE imager head for insertion into and movement through the esophagus of the patient. With the TEE imager head disposed in a target region within the esophagus, heat can be conveyed to the coupling member 1250 to expand and thereby release the coupling member 1250 from the TEE imager head 1130. With the coupling member 1250 released from the TEE imager head, the image capture assembly 1245 can be withdrawn from the patient, leaving the TEE device 1100 disposed within the patient (e.g., within the target region of the esophagus).

In some instances, the coupling member 1250 can include and/or define a sleeve configured to circumscribe at least in part the TEE imager head 1130. The sleeve can include any suitable release mechanism. For example, in some instances, the sleeve can include a threaded seam. In this manner, a portion of the thread can be configured to extend from the coupling member 1250 when the coupling member 1250 is disposed within, for example, the target region of the esophagus, through the esophagus and out the mouth of the patient such that an operator can pull or otherwise manipulate the thread to open the threaded seam. In some instances, the thread can be coupled to the retrieval tension member 1260, and the retrieval tension member 1260 can be pulled and/or otherwise manipulated to pull the thread a distance sufficient to open the threaded seam. With the threaded seam opened, the sleeve of the coupling member 1250 is allowed to release from the TEE imager head 1130. With the coupling member 1250 released from the TEE imager head 1130, the image capture assembly 1245 can be withdrawn from the patient, leaving the TEE device 1100 disposed within the patient (e.g., within the target region of the esophagus).

In yet further instances, in addition to or instead of the threaded seam, the sleeve of the coupling member 1250 can include a sliding mechanical fastener, such as a zipper. In such instances, the coupling member 1250 can be releasably coupled to the TEE imager head 1130 by sliding the sleeve about the TEE imager head 1130 and sliding or otherwise manipulating a slider of the zipper to transition the zipper to its engaged configuration. The slider of the sleeve can be operably coupled to the distal end portion of the retrieval tension member 1260. In use, for example, with the sleeve of the coupling member 1250 disposed about the TEE imager head, the zipper engaged, and the TEE imager head 1130 disposed in a target region with the patient, an operator can pull or otherwise manipulate the retrieval tension member 1260 (and/or the CAD handle 1280) to slide the slider a distance sufficient to release the sleeve from the TEE imager head 1130. With the sleeve disengaged from the TEE imager head 1130, the image capture assembly 1245 can be withdrawn from the patient, as described in more detail herein.

In some instances, the coupling member 1250 can be configured to not obstruct an imaging array of the TEE device 1100 when the coupling member 1250 is coupled to the TEE imager head 1130. In this manner, the coupling member 1250 can be configured to not compromise image data to be captured by the TEE device 1100. In other instances, for example, the coupling member 1250 can include an imaging window defined such that the imaging window does not obstruct the imaging array of the TEE device 1100 when the coupling member 1250 is coupled to the TEE imager head 1130. In yet further instances, for example, a portion of the coupling member 1250 can be transparent to energy (e.g., ultrasound) transmitted from and received by the imaging array to allow the energy to pass through the portion of the coupling member 1250 when the coupling member 1250 is releasably attached to the TEE imager head 1130. In this manner, the coupling member 1250 can be coupled to the TEE imager head 1130 without interfering with imaging operations of the TEE imager head 1130.

In some embodiments, for example, in which a coupling member is configured to be coupled to a TEE imager head without interfering with imaging operations of the TEE imager head, in use, the coupling member can remain coupled to the TEE imager head throughout the intubation procedure, including during removal of the TEE probe from the patient. In such instances, the image capture device can provide image data captured within the patient's digestive system during insertion of the TEE probe, and/or during removal of the TEE probe, with the image capture device attached to the TEE imager head.

In some instances, the image capture assembly 1245, or any portions thereof (e.g., the illumination device 12340, the image capture device 1240, the coupling member 1250), can be monolithically constructed, while in other instances, one or more of the portions of the image capture assembly 1245 can be formed separately and then joined together. Further, the image capture assembly 1245, or any portions thereof, can include one or more seals configured to withstand bodily fluid. For example, in some instances, it is important to seal the electronics of the image capture assembly 1245 (e.g., the image capture device 1240 and the illumination device 1230) from any potentially compromising bodily fluids (e.g., bodily fluids of the esophagus and/or the stomach of the patient). In this manner, the electronic components can be protected from such fluids.

During retrieval and removal of the CAD 1200 from the digestive system of the patient, it is desirable to limit and/or prevent excessive contact with the esophagus (e.g., trauma to the wall of the esophagus, esophageal and/or pharyngeal perforation) and associated anatomy by the CAD 1200. Said another way, with the coupling member 1250 decoupled from the TEE imager head, it is desirable to control and/or define at least in part a removal profile of the CAD 1200 from patient. To that end, the CAD 1200 can include a tension coupler 1270, as shown for example in FIGS. 2B and 2C, configured to slidably engage with the TEE body 1120 of the TEE device 1100. With the tension coupler 1270 slidably coupled to and/or engaged with the TEE body 1120, and with the TEE device 1100 and the CAD 1200 disposed in the esophagus and the coupling member 1250 of the CAD 1200 released from the TEE imager head 1130, the retrieval tension member 1260 can be controlled and/or retained close to the TEE body 1120 as the retrieval tension member 1260 is withdrawn proximally through the esophagus and out the mouth of the patient. In this manner, the CAD 1200 can be withdrawn through the esophagus in a controlled manner to limit and/or avoid undesirable contact with surrounding anatomy. Said another way, the tension coupler 1270 can define at least in part a removal profile of the CAD 1200 through the digestive system of the patient.

The tension coupler 1270 can include any suitable mechanism configured to slidably engage with the TEE body 1120 to control and/or define the removal profile of the CAD 1200 from the TEE device 1100 and the patient. For example, in some instances, the tension coupler 1270 can include one or more rings and/or straps configured to wrap around or otherwise be disposed about the TEE body 1120. In such instances, for example, as an operator pulls or otherwise manipulates the CAD handle 1280 and/or the retrieval tension member 1260 to withdraw the CAD 1200 from the patient, a distance between the retrieval tension member 1260 and the TEE body 1120 is defined and/or limited by a size (e.g., a diameter or perimeter) of the rings and/or straps.

In some instances, the tension coupler 1270 can include a magnetic mechanism configured to releasably attach to the TEE body 1120 by magnetic force. For example, the tension coupler 1270 can include one or more electromagnets configured to releasably attach to the TEE body by electromagnetic force when the one or more electromagnets are energized. Similar to the discussion with respect to the coupling member 1250 having an electromagnetic mechanism, the electromagnets of the tension coupler 1270 can be deenergized to release the tension coupler 1270 (and in turn at least a portion of the retrieval tension member 1260) from the TEE body 1120.

As described above, the image data captured by the image capture device 1240 can be conveyed to the graphical display device 1210 of the CAD 1200 via the communication line 1220, e.g., during TEE intubation. In some instances, the graphical display device 1210 can be the same device at which image data captured by the TEE device 1100 is displayed. In this manner, an operator can view both image data captured by the TEE device 1100 and the image capture device 1240 at a single graphical display device 1210. In other instances, the image data captured by the image capture device 1240 and the image data captured by the TEE device 1100 can be displayed at separate graphical display devices. For example, in such instances, the image data captured by the image capture device 1240 can be displayed at the graphical display device 1210, and the image data captured by the TEE device 1100 can be displayed at an echocardiography machine distinct and/or separate from the graphical display device 1210. In some instances, the graphical display device 1210 can be wearable by the operator. For example, in such instances, the graphical display device 1210 can include an eyepiece in which an operator can view in real-time (e.g., during the TEE intubation) the image data captured by the image capture device 1240 of the CAD 1200.

Figure 3:
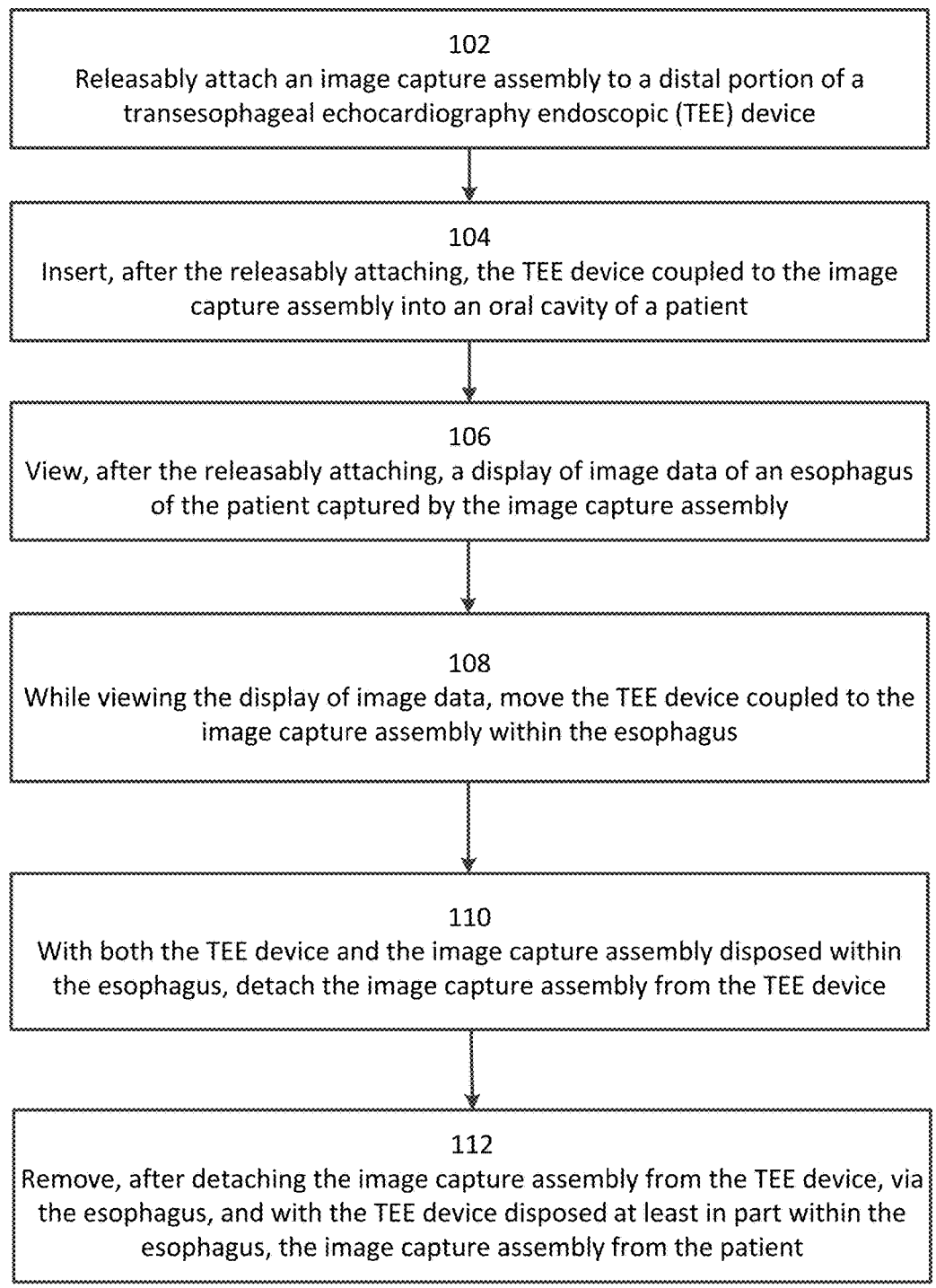
FIG. 3 is a flow chart of a method of assisting TEE intubation, according to an embodiment.

FIG. 3 shows a schematic flow diagram of a method of using a camera assist device (CAD) to assist an intubation procedure using a transesophageal echocardiography endoscopic (TEE) device, according to an embodiment. The method 100 includes releasably attaching an image capture assembly (the image capture assembly 1245 of the CAD 1200, or any other image capture assembly described herein) to a distal portion of a TEE device, at 102.

With the TEE device coupled to the image capture assembly, the method 100 further includes inserting, after the releasably attaching, the TEE device coupled to the image capture assembly into an oral cavity of a patient, at 104. The method 100 further includes viewing, after the releasably attaching, a display of image data (e.g., a graphical representation) of an esophagus of the patient captured by the image capture assembly, at 106. The method 100 further includes moving, while viewing the display of image data, the TEE device coupled to the image capture assembly within the esophagus, at 108. In this manner, an operator can visualize insertion of TEE device into the patient to avoid, for example, undesirable perforations of tissue therein. The method 100 further includes detaching, with both the TEE device and the image capture assembly disposed within the esophagus of the patient, the image capture assembly from the TEE device (e.g., the TEE imager head of the device), at 110. The method 100 further includes removing, after the detaching the image capture assembly from the TEE device, via the esophagus, and with the TEE device disposed at least in part within the esophagus, the image capture assembly from the patient, at 112.

FIGS. 4-13 illustrate an embodiment of a CAD 2200 that can be used to assist intubation of a TEE probe (also referred to herein as "TEE device"). As shown schematically in side view in FIG. 4, the CAD 2200 is removably attached to the TEE probe 2100. The TEE probe 2100 includes a TEE body 2120 having a TEE imager head 2130 coupled to its distal end and a TEE controller (not shown) coupled to its, opposite, proximal end. The TEE imager head 2130 includes an imaging array 2132 configured to capture image data of, for example, a heart of the patient. For example, with the imager head 2130 disposed within the esophagus of a patient, the imager head 2130 can be configured to transmit ultrasound waves to the heart and receive waves deflecting and/or rebounding therefrom. An image processor (not shown) can transform the image data (e.g., ultrasound waves) and transmit the transformed data to a visual display (not shown) outside the patient. In this manner, with the TEE imager head 2130 disposed within the patient (e.g., within the esophagus of the patient), an operator (e.g., a cardiologist) can view from outside the patient a graphical representation of the heart and surrounding anatomy inside the patient.

Figure 4:
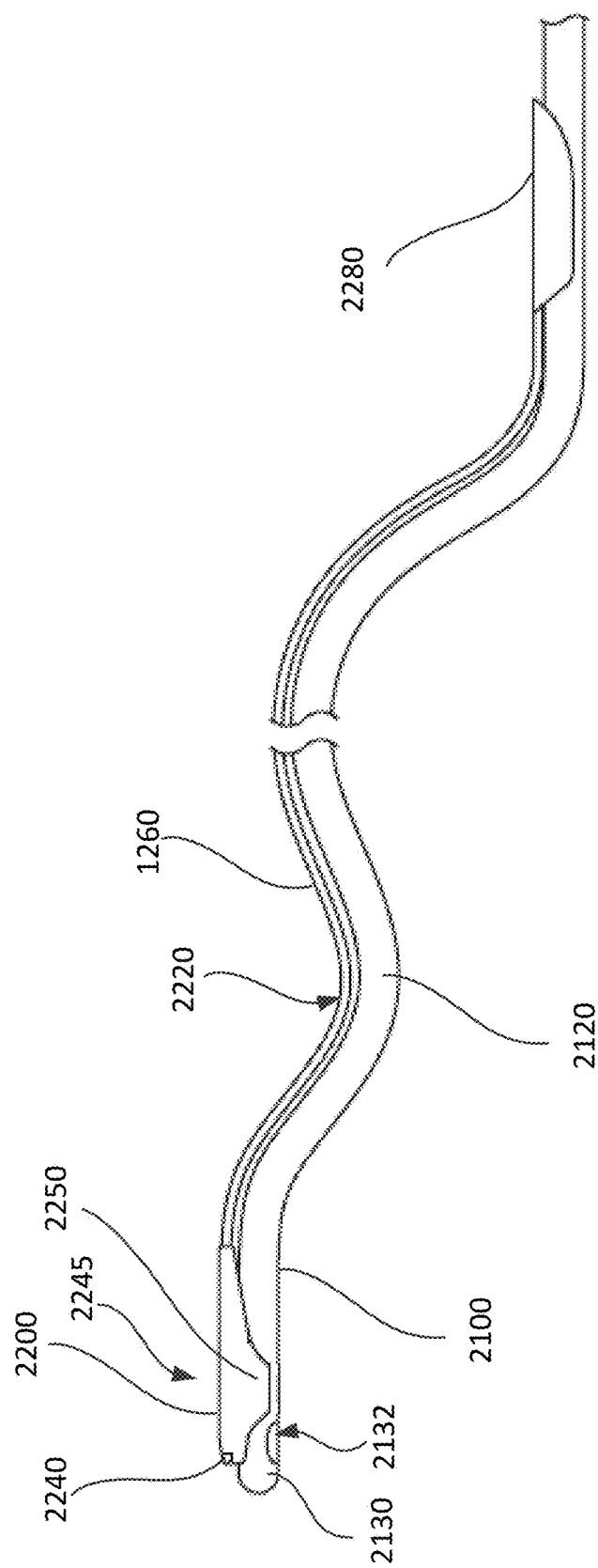
FIG. 4 is a schematic illustration of a portion of a CAD releasably attached to a portion of a TEE device, according to an embodiment.

To facilitate such insertion of the TEE imager head 2130, the CAD 2200 can be removably coupled to the TEE imager head 2130 (as shown by FIG. 4) prior to and during the insertion into and passage through the esophagus of the patient to provide the operator with real-time images of the passageway and surrounding anatomy. With access to such real-time images, the operator can limit or avoid undesirable and/or inadvertent contact with the esophagus and/or associated anatomy, thereby limiting and/or preventing complications, and in extreme circumstances, mortality. Additionally, with such access to real-time images, the operator can easily and repeatedly locate various regions of interest within the esophagus in which to dispose the TEE imager head 2130 for imaging of the heart and other anatomy. After assistance from the CAD 2200 in moving the TEE imager head 2130 in the esophagus to a target region of the esophagus (e.g., a region in which the TEE imager head 2130 can send signals to and receive signals from target anatomy, such as the heart), the CAD 2200 can be decoupled and/or removed from the TEE imager head 2130. With the CAD 2200 decoupled from the TEE imager head 2130, the CAD 2200 can be withdrawn proximally through the esophagus 24, oral cavity 22, and out the mouth 21 of the patient, leaving the TEE imager head 2130 disposed within the target region of the esophagus 24.

In this embodiment, the CAD 2200 includes an image capture device 2240 configured to capture image data within a digestive system of a patient, and a coupling member 2250 configured to releasably attach to the TEE imager head 2130 of the TEE device 2100 (the image capture device 2240 and the coupling member 2250 collectively referred to herein as "image capture assembly 2245"). FIGS. 8A-8F illustrate various detailed views of the image capture assembly 2245.

As discussed in further detail herein, the image capture device 2240 can be configured to send the image data it captures across a communication line 2220 extending from the image capture device 2240 to a graphical display device 2210. The graphical display device 2210 can be configured to display a graphical representation of the image data, thereby providing an operator of the TEE device 2100 with visual access in real-time to various portions within the digestive system of the patient.

Figure 5:
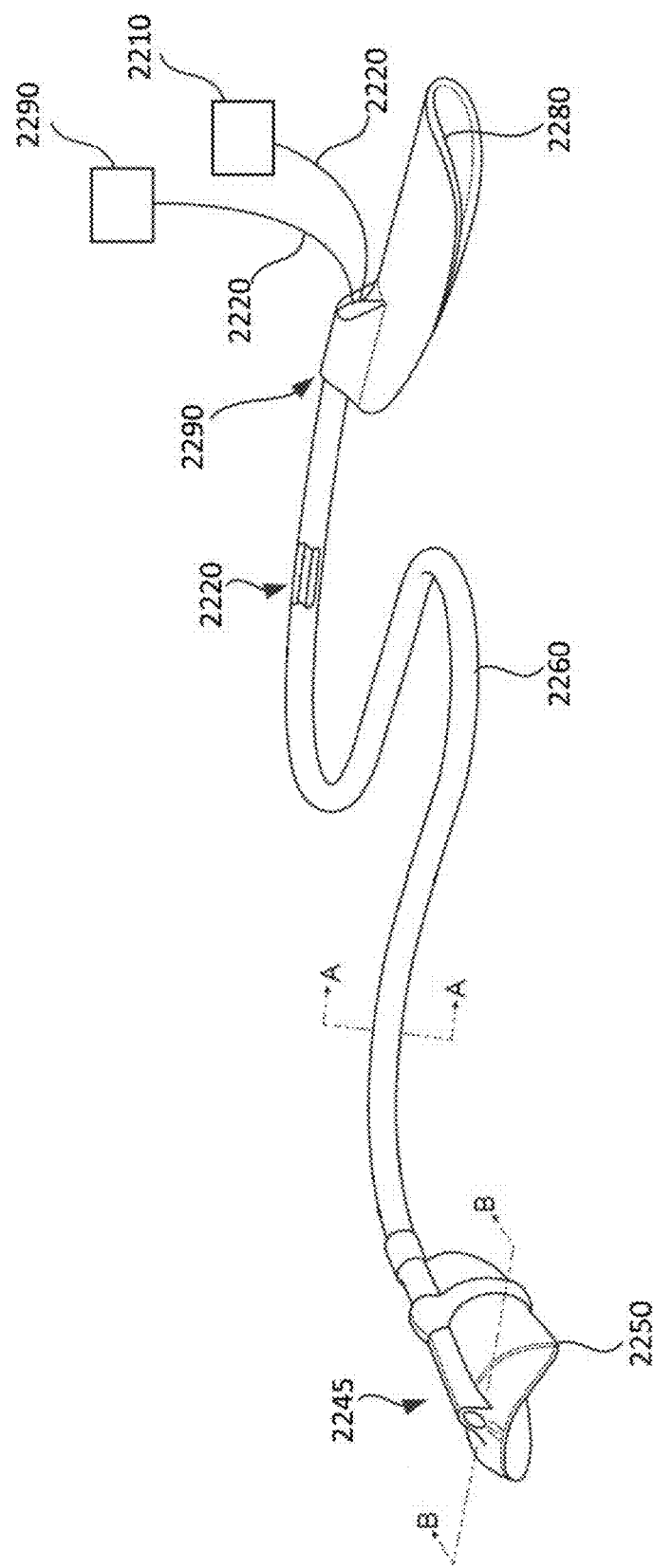
FIG. 5 is a perspective view of the CAD of FIG. 4.
Figure 7:
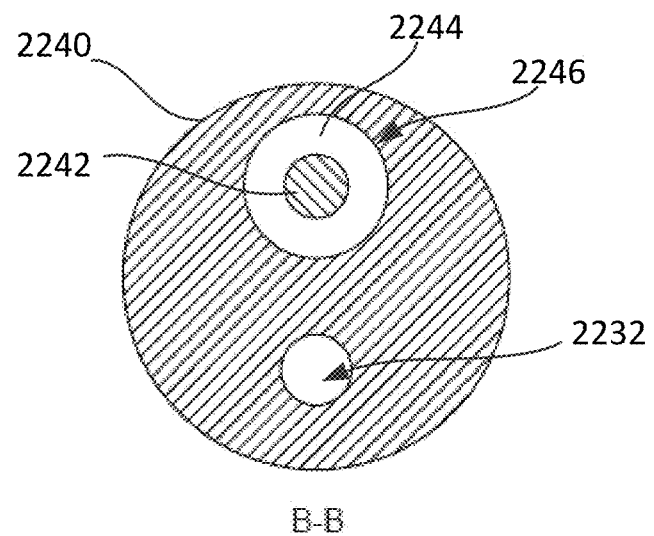
FIG. 7 is a cross-sectional view of an image capture assembly of the CAD of FIG. 4, taken along the line B-B.
Figure 8A:
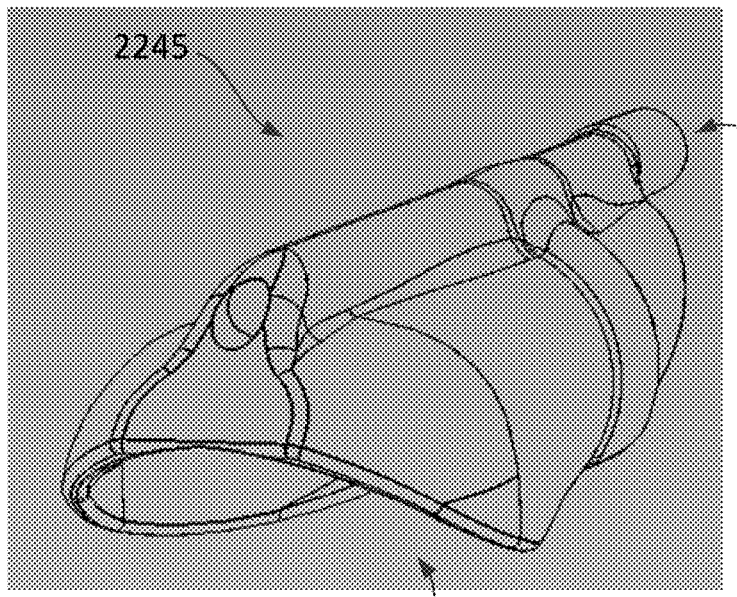
FIGS. 8A-8F are perspective, top, bottom, back, front, and side views, respectively, of the image capture assembly of FIG. 7.
Figure 8B:
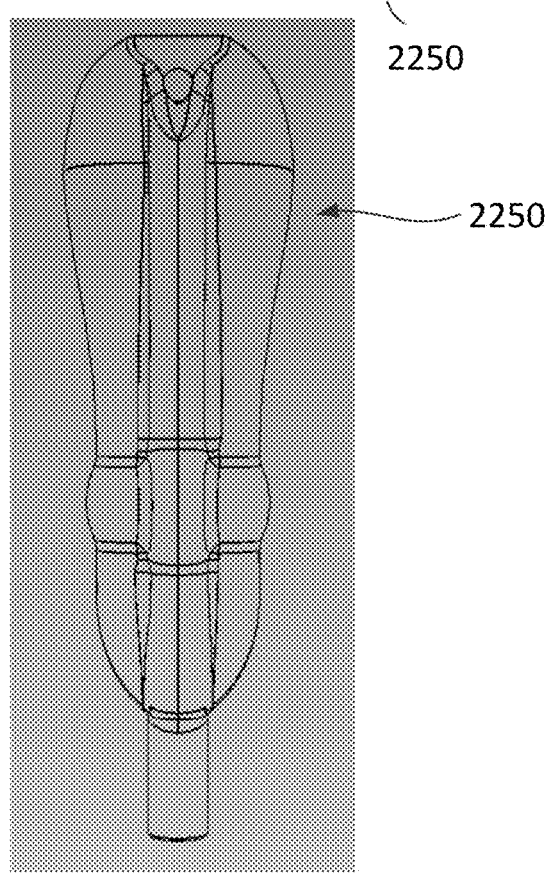
Figure 8C:
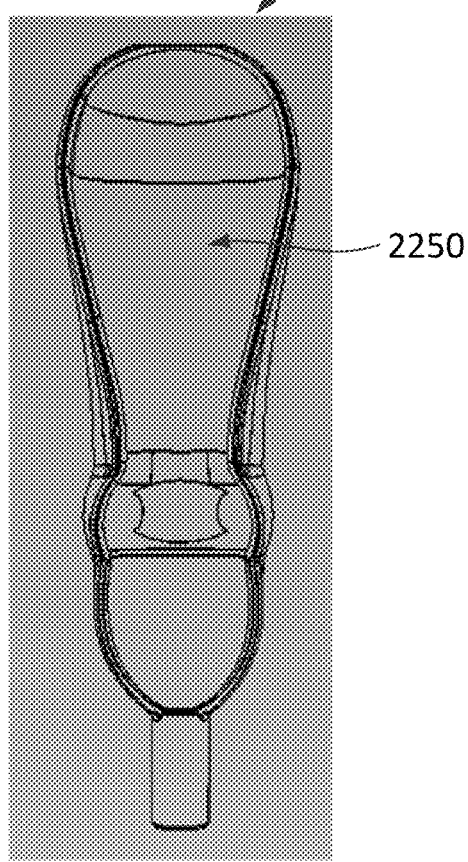
Figure 8D:
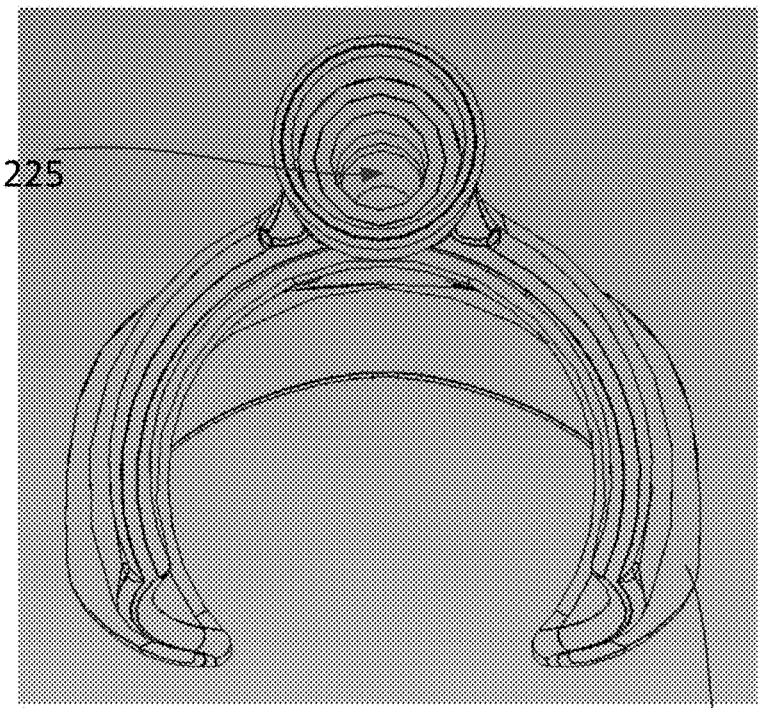
Figure 8E:
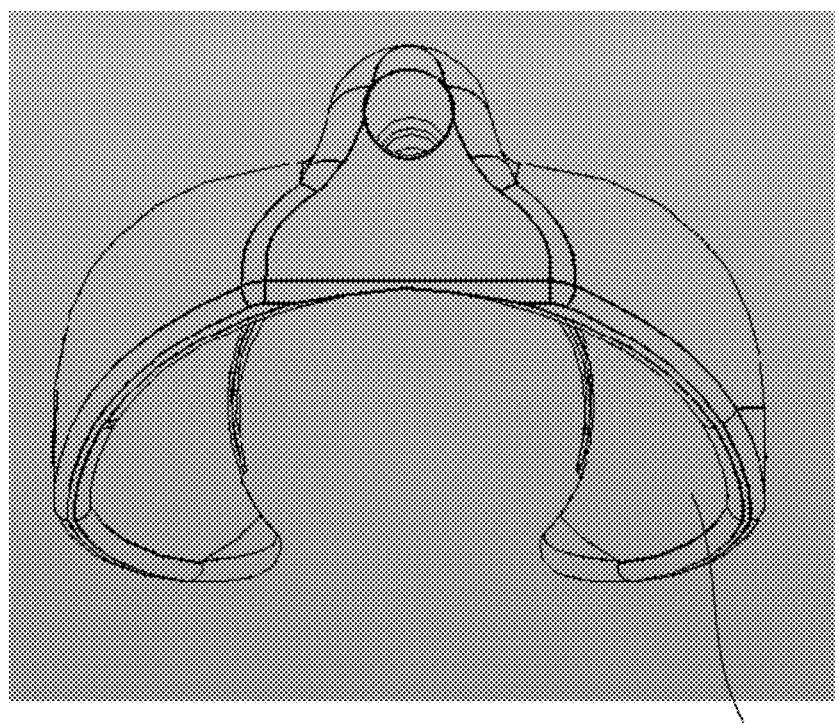
Figure 8F:
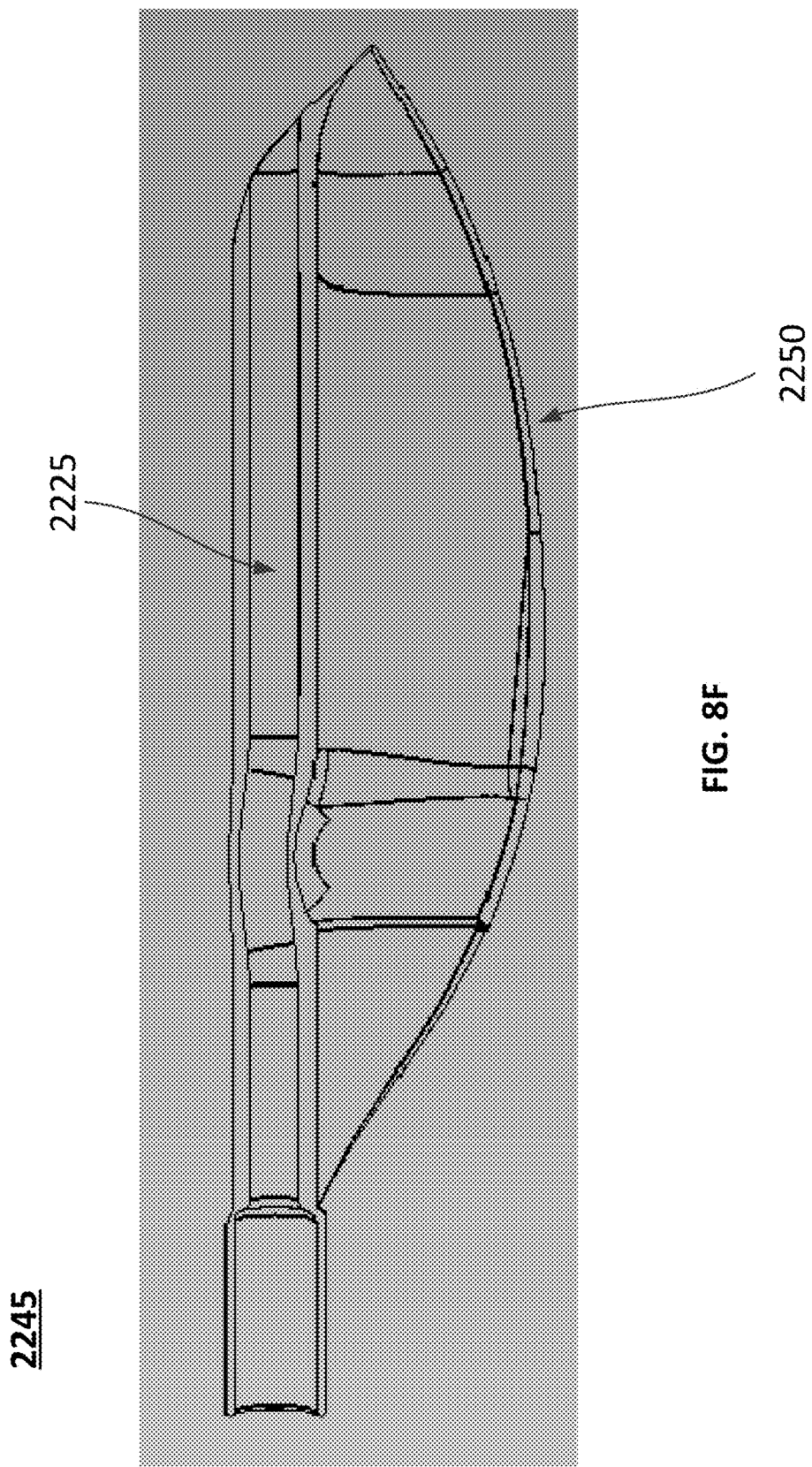

The image capture device 2240 includes a sensor 2242 and a lens 2244, and is configured to transmit image data captured within the patient to the graphical display device 2210 disposed outside the patient via the communication line 2220, as shown in FIG. 5. As shown, the lens 2244 is disposed at a distal end portion of the image capture assembly 2245. In this manner, the image capture device 2240 can capture image data immediately distal to and/or immediately downstream of the image capture assembly 2245. FIG. 7 shows the cross-sectional view identified as B-B in FIG. 5 of the image capture device 2240. As shown in FIG. 7, the image capture device 2240 defines an aperture 2246 through in which the lens 2244 is disposed, and the lens defines a pathway through which the sensor 2242 can communicate with a target area to capture image data. Also as shown, the image capture device defines an illumination aperture 2232 through which the illumination device 2230 can communicate to illuminate at least a portion of the target area.

In some instances, the image capture device 2240 can include an image processor (not shown) configured to process the image data such that the image data can be graphically displayed on the graphical display device 2210. In other instances, for example, to allow for a smaller form factor of the image capture device 2240, processing of the image data can occur entirely outside the patient and distinct from the image capture device 2240. In such instances, the image data can be processed, for example, at an image processor of the graphical display device 2210. In yet further instances, the image data can be processed at an image processor separate from both the graphical display device 2210 and the image capture device 2240, and the sent to the graphical display device 2210 to be displayed. In some instances, the image capture device 2240 can include wireless capabilities. For example, in such instances, the image capture device 2240 can communicate wirelessly with an image processor and/or the graphical display device 2210. In this manner, image data can be transmitted from the image capture device 2240 when disposed within the patient to outside the patient without any physical wires.

In some instances, the image capture device 2240 can be controlled remotely via the communication line 2220. For example, in such instances, the image capture device 1240 can receive via the communication line 2220 a signal including instructions to capture one or more images. In some instances, the image capture device 2240 can receive power via the communication line 2220 from a power source external to patient. In other instances, the image capture device 2240 can include a power source (e.g., a battery) configured to store power sufficient for operation of the image capture device 2240. As shown best by FIG. 8F in cross-sectional side view, the image capture assembly 2245 defines a communication lumen 2225 through which the electronics of the image capture device 2240 can communicate with the communication line 2220.

In some instances, the image capture device 2240 can include a lens filter (e.g., ultraviolet filter, infrared filter, etc.) (not shown). An image filter can provide an operator of the CAD 2200 visual indicators within the patient's digestive system. For example, in some instances, when moving the CAD 2200 within the patient, an operator may want to avoid certain weak portions (or portions otherwise particularly susceptible to damage and/or trauma) of the digestive system (e.g., esophagus). In such instances, a lens filter can provide visual indicators to the operator when a graphical representation of the image data is displayed.

Figure 6:
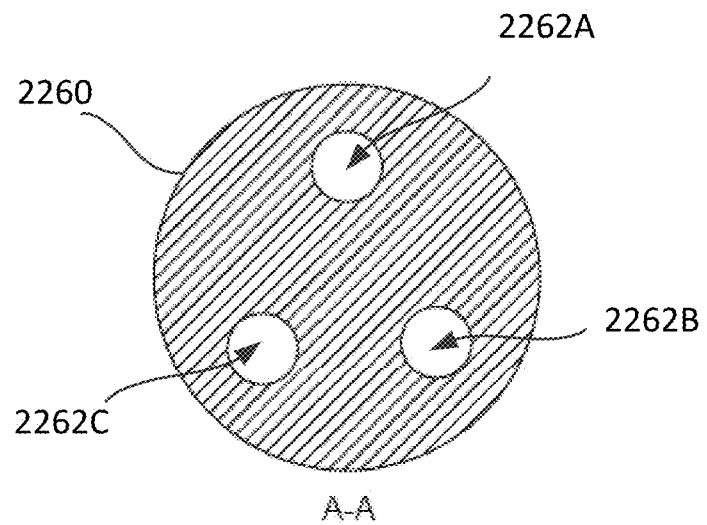
FIG. 6 is a cross-sectional view of a retrieval tension member of the CAD of FIG. 4, taken along the line A-A.

The CAD 2200 further includes a retrieval tension member 2260 that is operable to decouple the image capture assembly 2245 of the CAD 2200 from the TEE imager head 2230. As shown, a distal end portion of the retrieval tension member 2250 is coupled to the coupling member 2250 of the CAD 2200, and an opposite, proximal end portion of the retrieval tension member 2260 can be coupled to a CAD handle 2280. FIG. 6 shows the cross-sectional view identified as A-A in FIG. 5 of the retrieval tension member 2260. As shown in FIG. 6, the retrieval tension member 2260 defines multiple tension member lumens through which the communication line 2220 is routed. In this embodiment, the retrieval tension member 2260 defines three tension member lumens, i.e., 2262A, 2262B, and 2262C, however, in alternative embodiments, the retrieval tension member 2260 can define any suitable number of lumens. In this embodiment, for example, the communication line 2220 can include an image data wire, a power wire, and an illumination wire, each of which can be routed through one of the tension member lumens 2262A, 2262B, 2262C. In embodiments in which a retrieval tension member includes one or more electromagnetic tension couplers, the communication line can include one or more electromagnetic actuation wires that can be routed through one or more of the tension member lumens 2262A, 2262B, 2262C.

As shown in FIG. 5, a portion (e.g., an image data wire) of the communication line 2220 can be routed through a communication lumen 2285 of the CAD handle 2280 and communicatively coupled to the graphical display device 2210. Further, a portion (e.g., a power wire, an illumination wire, etc.) of the communication line 2220 can be routed through communication lumen 2285 of the CAD handle 2280 and communicatively coupled to a CAD controller 2290. The CAD controller 2290 is operable (e.g., by an operator) to control the electronic components of the CAD 2200. For example, a user can manipulate the CAD controller 2290 to instruct the image capture device 2240 to capture one or more images. As another example, the CAD controller 2290 is operable to send power to the image capture device 2240 and/or the illumination device 2230. In alternative embodiments in which the retrieval tension member 2260 includes electromagnetic tension couplers, the CAD controller can be operable to energize and/or deenergize the electromagnetic tension couplers.

The CAD handle 2280 is removably coupled to a proximal portion of the TEE body 2120, and can be used to hold and/or control the retrieval tension member 2260 extending from the CAD controller 2280 during TEE intubation and removal of the CAD 2200 from the patient. In some instances, for example, in use, the CAD handle 2280 can be removably coupled to the TEE device 2100 (as shown in FIG. 4) during TEE intubation and until the operator is ready to withdraw the CAD 2200 from the patient. In this manner, undesirable slack in the retrieval tension member 2260 and/or in the communication line 2220 can be limited and/or avoided. Said another way, with the coupling member 2250 removably coupled to the TEE imager head 2130, the CAD handle 2280 can be pulled such that the retrieval tension member 2260 is substantially taught. With the retrieval tension member 2260 substantially taught, the CAD handle 2280 can be removably coupled to the proximal portion of the TEE body 2120, as shown in FIG. 4.

Further, as shown in FIG. 4, the communication line 2220 is routed through a lumen of the retrieval tension member 2260. In this manner, the communication line 2220 extending from the image capture assembly 2245 to the CAD handle 2280 can be shielded or otherwise protected by the retrieval tension member 2260. Although not shown, the CAD handle 2280 can include an aperture through which the communication line 2220 can be routed. From the CAD handle 2280, the communication line 2220 can be routed to any suitable device (e.g., an image processor, the graphical display device 2210, a power source, etc.).

As shown, the image capture assembly 2245 of the CAD 2200 is configured to removably attach to the TEE imager head 2130 via the coupling member 2250. The coupling member 2250 includes a concave portion configured to receive and/or circumscribe at least in part a portion of the TEE imager head 2130. By receiving a portion of the TEE imager head 2130 in the concave portion of the coupling member 2250, the combined cross-sectional area of the TEE imager head 2130 and the image capture assembly 2245 of the CAD 2200 can be desirably small while providing coupling retention forces sufficient to maintain coupling between the TEE imager head 2130 and the coupling member 2250 during movement of the TEE device 2100 and CAD device 2200 through the patient's digestive system. In this embodiment, the coupling member 2250 is configured to releasably attach to the TEE imager head 2130 by an interference fit. In this manner, with the coupling member 2250 releasably attached to the TEE imager head 2130, the coupling member 1250, due to the interference fit, is configured to resist release from the TEE imager 2130 in response to forces falling short of a threshold force. As such, the coupling member 2250 can be configured to remain attached to the TEE imager head 2130 during insertion into and movement through the patient. For example, from insertion through the mouth through the larynx and to the esophagus of a patient, in some instances, the coupling member 2250 may experience its greatest forces as it moves through the larynx, as the larynx often includes the smallest diameter lumen and sharpest turn in TEE intubation procedures (e.g., in a normally functioning digestive tract). With such design considerations, the coupling member 2250 can be configured to withstand such forces without undesirably releasing from the TEE imager head 2230.

Further, in response to forces exceeding the threshold force, the coupling member 2250 can be configured to release from the TEE imager head 2230. For example, in use, a user can pull, withdraw, or otherwise manipulate the CAD handle 2280 to apply a longitudinal proximal force (via the retrieval tension member 2260) to the coupling member 2250 exceeding the threshold force, thereby causing the coupling member 2250 to decouple from the TEE imager head 2130. In some instances, the coupling member 2250 can be configured resist a threshold force up to about 10 N. In other instances, the coupling member 2250 can be configured to resist a threshold force up to about 15 N.

Further, as shown in FIG. 4, the coupling member 2250 is configured to releasably attach to the TEE imager head 2230 without obstructing the imaging array 2132 of the TEE device 2100. In this manner, the TEE device 2100 and the CAD 2200 can capture image data simultaneously when the coupling member 2250 is releasably attached to the TEE imager head 2130.

As described with respect to other embodiments herein, the image data captured by the image capture device 2240 can be conveyed to the graphical display device 2210 of the CAD 2200 via the communication line 2220, e.g., in real-time during TEE intubation. In some instances, the graphical display device 2210 can be the same device at which image data captured by the TEE device 2100 is displayed. In this manner, an operator can view both image data captured by the TEE device 2100 and the image capture device 2240 at a single graphical display device. In other instances, the image data captured by the image capture device 2240 and the image data captured by the TEE device 2100 can be displayed at separate graphical display devices. For example, in such instances, the image data captured by the image capture device 2240 can be displayed at a first graphical display device (e.g., the graphical display device 2210), and the image data captured by the TEE device 2100 can be displayed at a second graphical display device (e.g., an echocardiography machine) distinct and/or separate from the first graphical display device. In some instances, the first and/or second graphical display device can be wearable by the operator. For example, in such instances, the first and/or second graphical display device can include an eyepiece in which an operator can view in real-time (e.g., during the TEE intubation) the image data captured by the image capture device 2240 of the CAD 2200 and/or the image data captured by the TEE imager head 2130 of the TEE device 2100.

Figure 10:
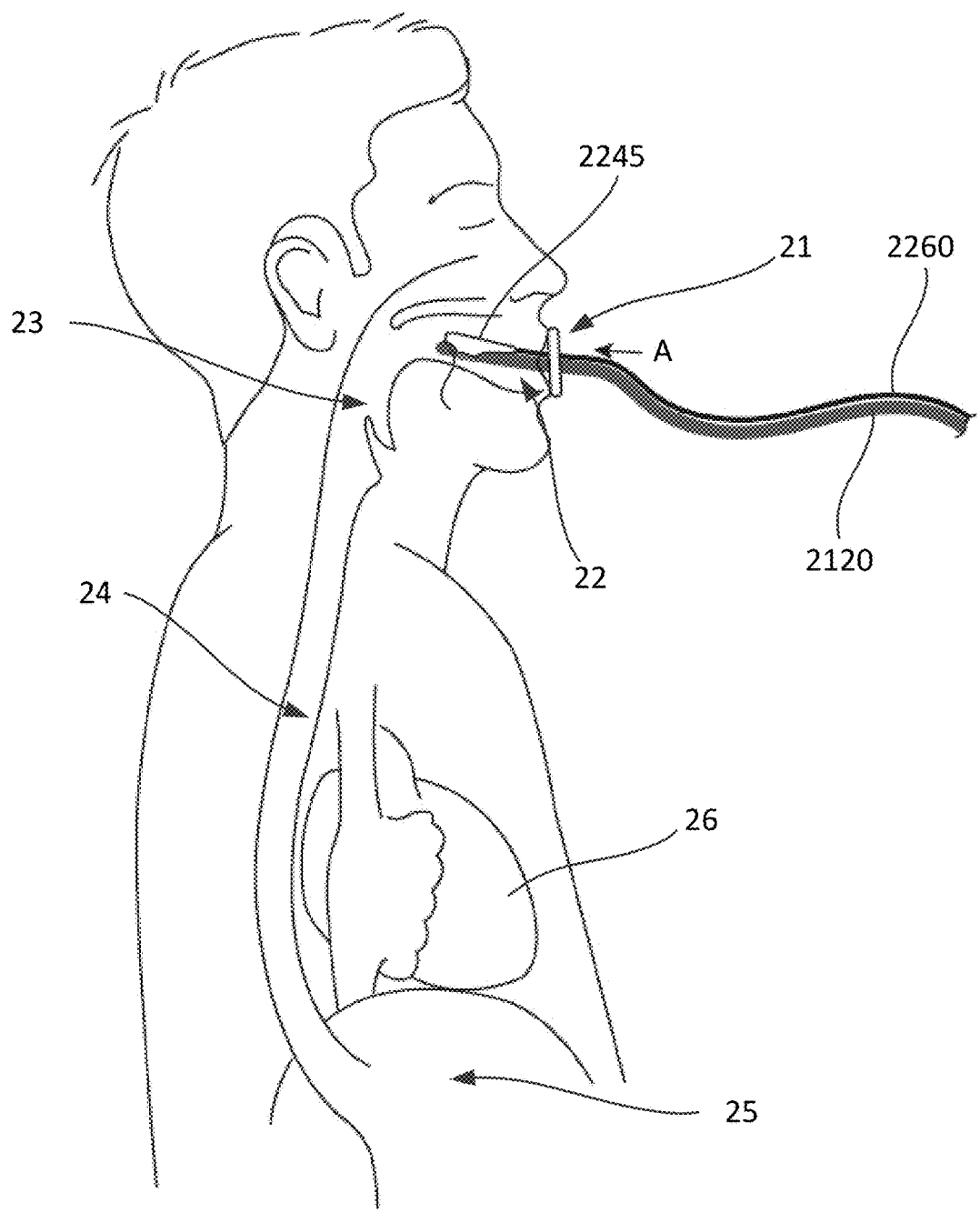
FIGS. 10-13 are schematic illustrations of the CAD of FIG. 4 in various stages of assisting a TEE intubation.
Figure 11:
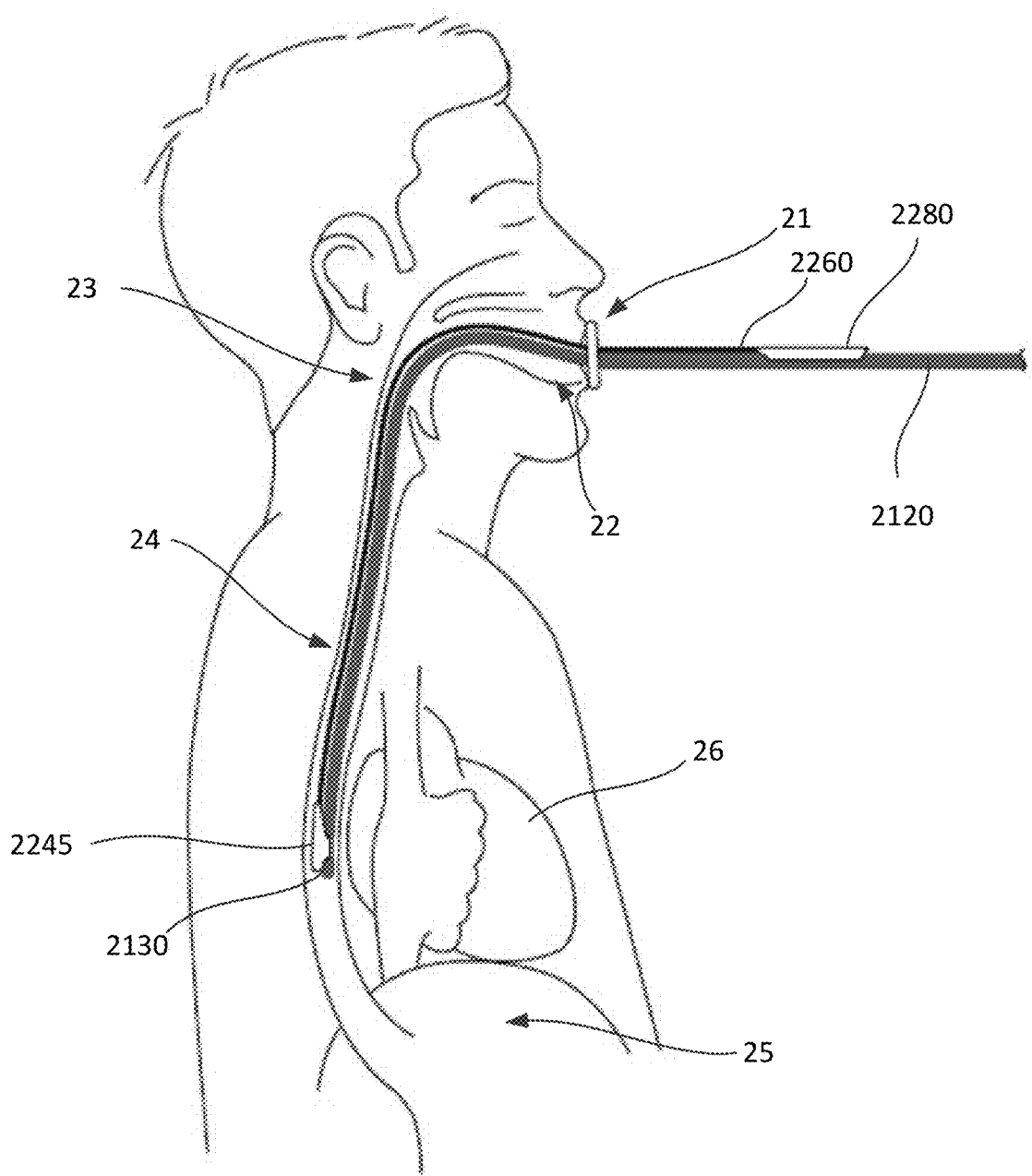

In use, to assist intubation of the TEE probe 2100, the image capture assembly 2245 of the CAD 2200 is removably attached to the TEE imager head 2130 of the TEE device 2100, and inserted with the TEE imager head 2130 into the mouth 21 of the patient, as shown in FIG. 10. As described in further detail herein, the image capture device 2240 of the image capture assembly 2245 is configured to capture and send image data in real-time (i.e., during the intubation procedure) to the graphical display device 2210 disposed outside the patient. With access to a graphical illustration of such image data, and with the image capture assembly 2245 inserted through the mouth 22, the operator can move (in the direction illustrated by arrow A) the TEE imager head 2130 and the image capture assembly 2245 toward and through the oral cavity 22 of the patient. Further, while viewing a real-time graphical representation of the patient's anatomy surrounding and/or downstream of the image capture assembly 2250 and the TEE imager head 2230, the operator can move the TEE imager head 2130 distally towards and into the esophagus 24 of the patient until the TEE imager head 2130 reaches a target region (as evidenced by the graphical representation of the image data captured by the image capture device 2240), as shown in FIG. 11. Although not shown in FIG. 11, the operator can move the TEE imager head 2130 further distally and dispose the TEE imager head 2130 in the patient's stomach 25.

Figure 12:
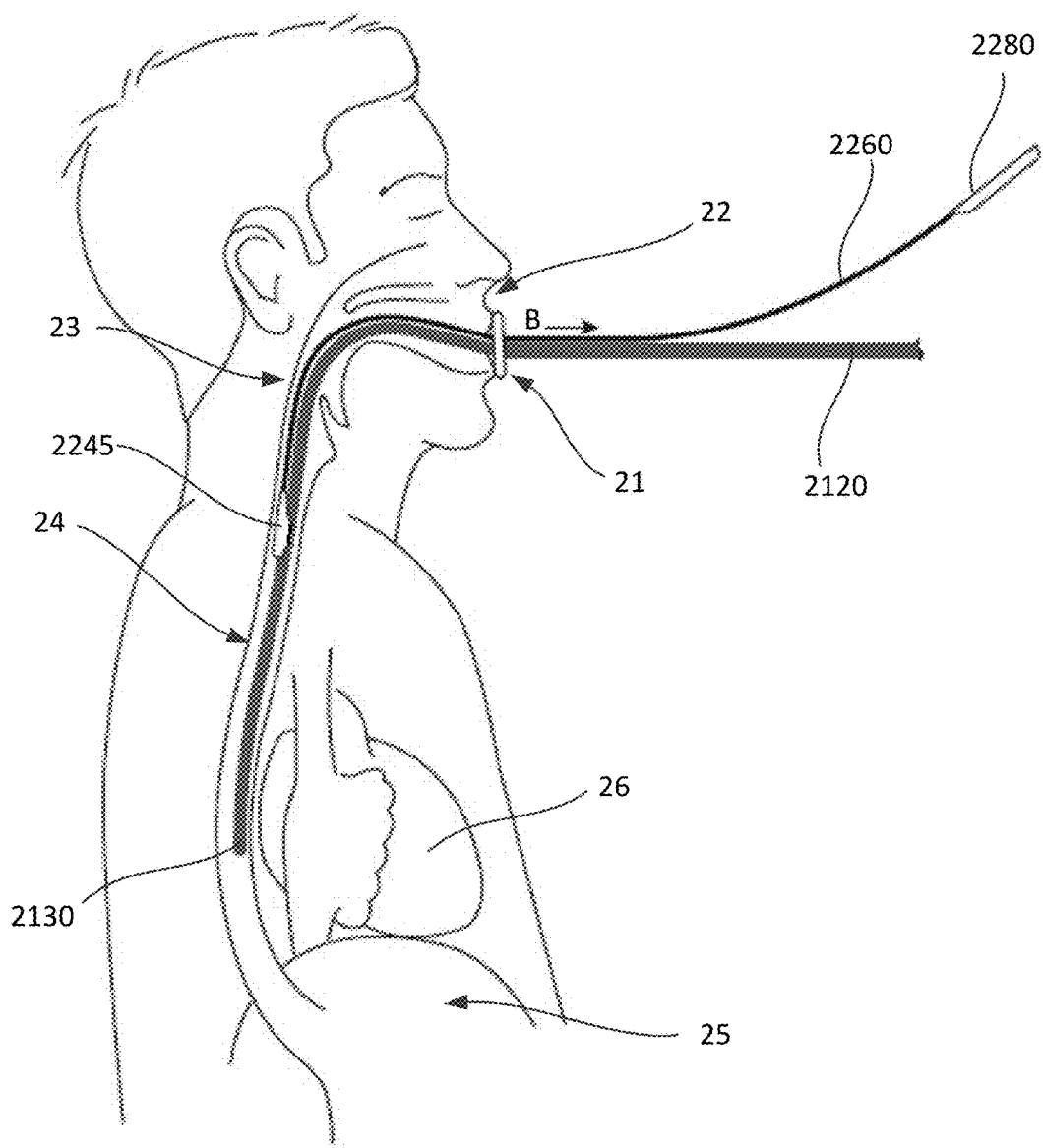
Figure 13:
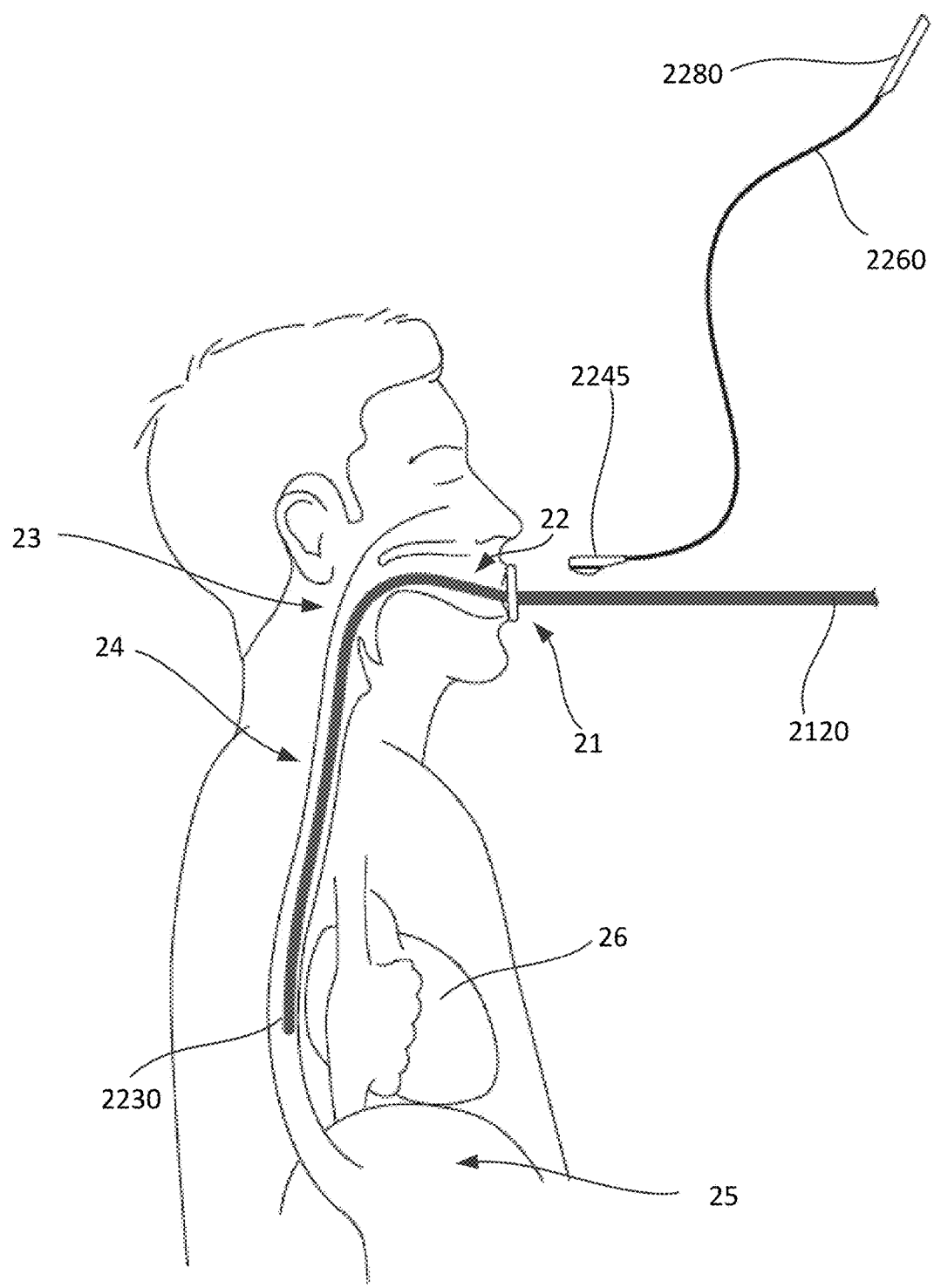

With the TEE imager head 2130 located within the target region of the esophagus, the operator can decouple the CAD handle 2280 from the TEE body 2220, and pull the CAD handle 2280 proximally to release the coupling member 2250 from the TEE device 2100, as described in further detail above. As shown in FIG. 12, with the coupling member 2250 released from the TEE device 2100, the operator can further pull the CAD handle 2280 proximally (in the direction illustrated by arrow B) such that the retrieval tension member 2260 and the image capture assembly 2245 are withdrawn proximally through the esophagus 24 of the patient, leaving the TEE imager head 2130 disposed within the target region of the esophagus 24, as shown in FIG. 12. As shown in FIG. 13, the operator can further pull the CAD handle 1280 proximally to remove the CAD 2200 entirely from the patient.

FIGS. 14-19 illustrate an embodiment of a CAD 3200 that can be used to assist intubation of a TEE probe (also referred to herein as "TEE device"). The CAD 3200 can be constructed and function similar to any of the CADs described herein, e.g., the CAD 1200, the CAD 2200, etc.). Thus, some details regarding the CAD 3200 are not described below. It should be understood that for features and functions not specifically discussed, those features and functions can be the same as or similar to any of the CADs described herein.

Figure 14:
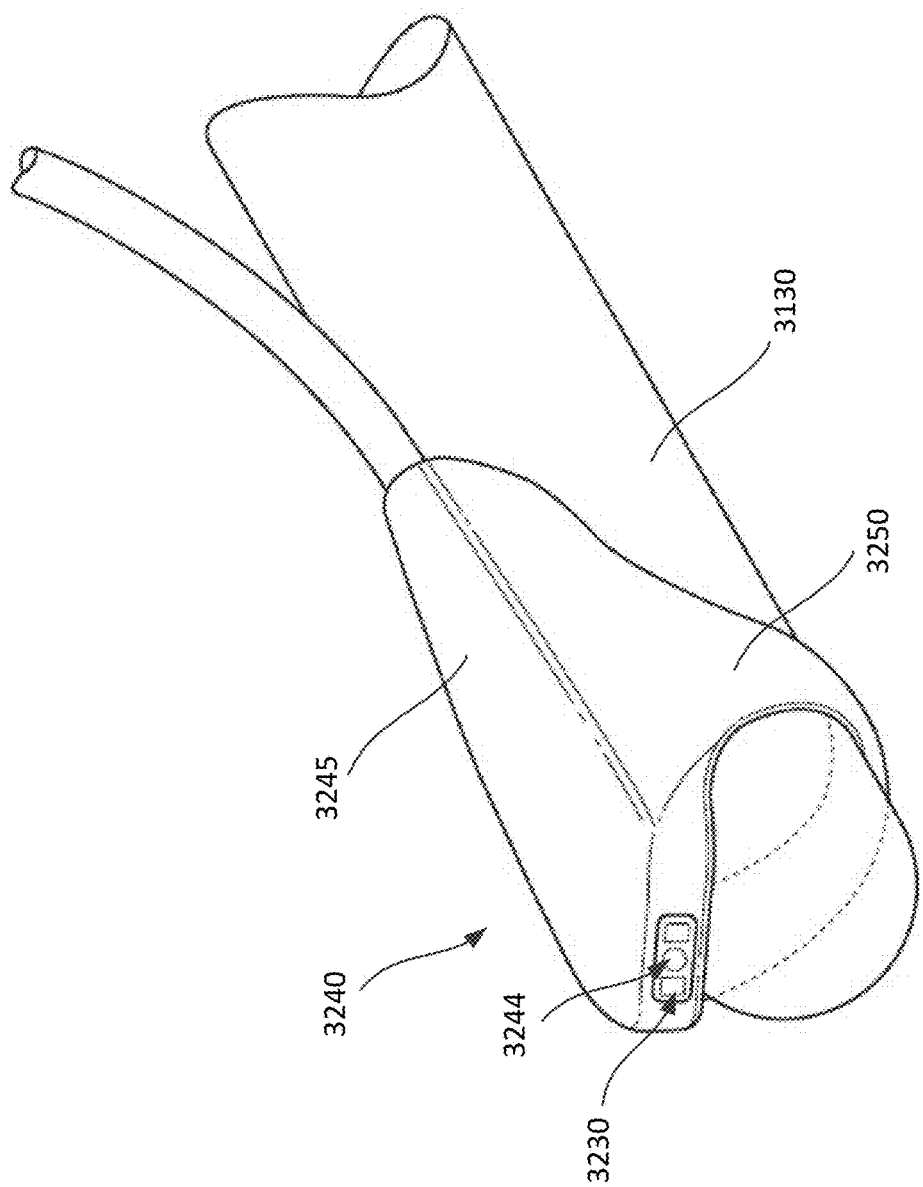
FIG. 14 is a perspective view of a portion of an image capture assembly of a CAD releasably attached to a portion of a TEE device, according to an embodiment.
Figure 15:
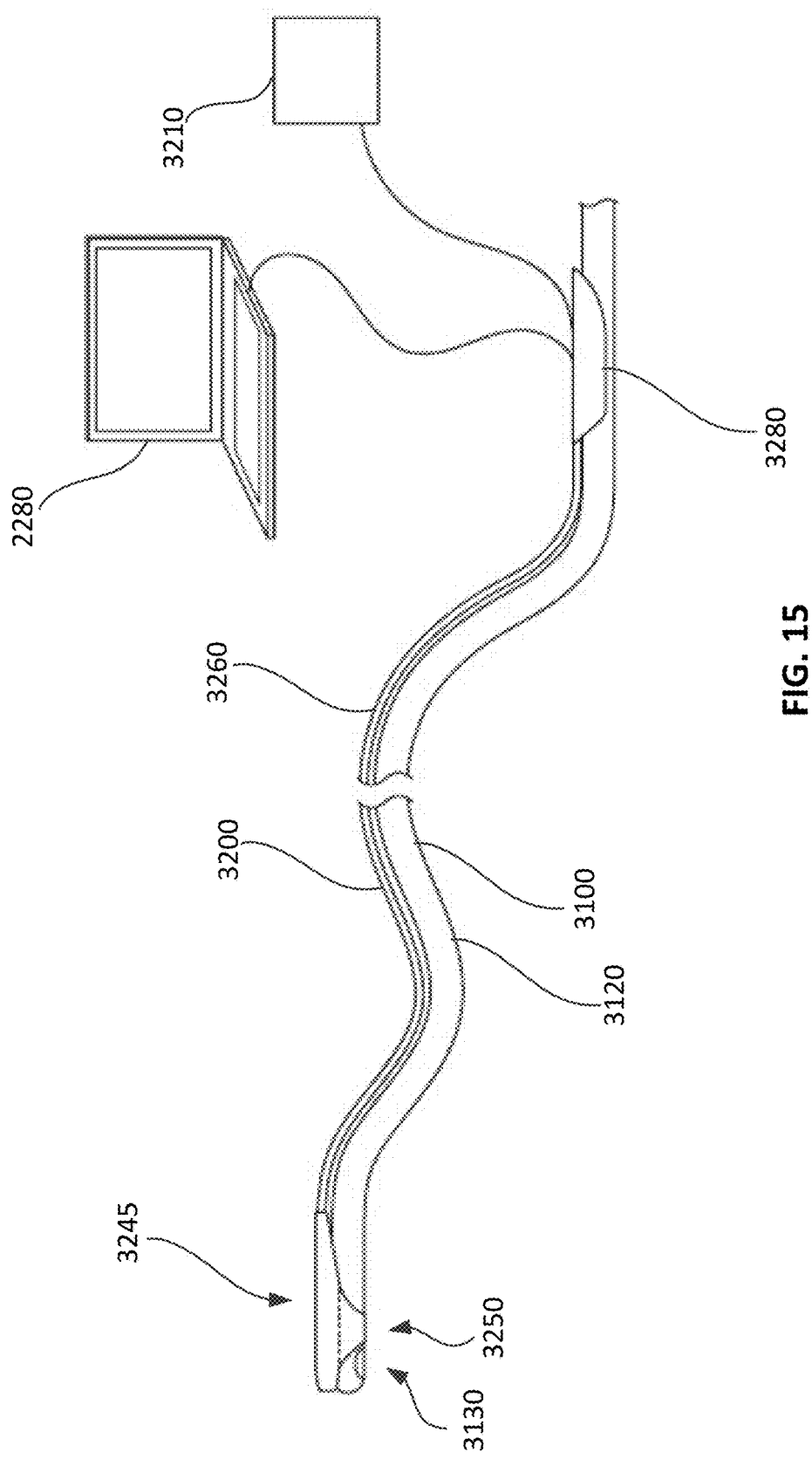
FIG. 15 is a schematic illustration of the CAD of FIG. 14 attached to the TEE device of FIG. 14.

As shown in FIG. 14, the CAD 3200 includes an image capture assembly 3245 configured to be removably coupled to a TEE imager head 3130 of a TEE device 3100. Similar to previous embodiments, the image capture assembly 3245 includes an illumination device 3230, an image capture device 3240 having a lens 3244, and a coupling member 3250. As shown, the image capture assembly 3245 is disposed about the TEE imager head 3130 such that the lens 3244 is aligned with the distal end of the TEE imager head 3130. In this manner, the image capture device 3240 can capture image data immediately distal and/or adjacent to the distal end of the TEE imager head 3130. In alternative embodiments, an image capture assembly can be disposed about a TEE imager head such that a lens of the image capture assembly is aligned distal to the distal end of the TEE imager head. In this embodiment, the coupling member 3250 defines a sleeve configured to entirely circumscribe a portion of the TEE imager head 3130, as shown in FIG. 14.

In some instances, the sleeve of the coupling member 3250 can be configured to not obstruct an imaging array (not shown) of the TEE device 3100 when the coupling member 3250 is coupled to the TEE imager head 3130, as shown in FIG. 14. In this manner, the coupling member 3250 can be configured to not compromise image data to be captured by the TEE device 3100. In other instances, for example, the sleeve of the coupling member 3250 can define an imaging window such that the imaging window does not obstruct the imaging array of the TEE device 3100 when the coupling member 3250 is coupled to the TEE imager head 3130. In this manner, the TEE imager head 3130 can capture image data conveyed through the imaging window of the coupling member 3250 when the coupling member 3250 is releasably attached to the TEE imager head 3130. In yet further instances, for example, a portion of the coupling member 1250 can be transparent to energy (e.g., ultrasound) transmitted from and received by the imaging array to allow the energy to pass through the portion of the coupling member 1250 when the coupling member 1250 is releasably attached to the TEE imager head 1130.

With the coupling member 3250 releasably attached to the TEE imager head 3130, the coupling member 3250 can provide a friction fit with the TEE imager head 3130 such that the coupling member 3250 can resist longitudinal movement relative to the TEE imager head 3120 in response to a force below a threshold force, similarly as described with respect to previous embodiments. For example, the coupling member 3250 can be configured to remain releasably attached to the TEE imager head 3130 during insertion into and movement through the patient. For example, from insertion through the mouth through the larynx and to the esophagus of the patient, in some instances, the coupling member 3250 may experience its greatest forces as it moves through the larynx, as the larynx often includes the smallest diameter lumen and sharpest turn in such TEE intubation procedures (e.g., in a normally functioning digestive tract). With such design considerations, the coupling member 3250 can be configured to withstand such forces without undesirably releasing from the TEE imager head 3230.

Further, in response to a force (e.g., a longitudinal force in the proximal direction) exceeding the threshold force, the coupling member 3250 can be configured to release from the TEE imager head 3230. For example, in use, a user can pull, withdraw, or otherwise manipulate the CAD handle 3280 to apply a longitudinal proximal force (via the retrieval tension member 3260) to the coupling member 3250 exceeding the threshold force, thereby causing the sleeve of the coupling member 3250 to overcome the frictional forces between the sleeve and the TEE imager head 3130 such that the coupling member slides proximally relative to the TEE imager head 3130. In some instances, the coupling member 3250 can be configured to resist a threshold force up to about 10 N. In other instances, the coupling member 3250 can be configured to resist a threshold force up to about 15 N.

In some instances, the sleeve of the coupling member 3250 can be formed of a flexible material. In such instances, when decoupling the coupling member 3250 from the TEE imager head 3130 (e.g., causing the coupling member 3250 to slide proximally about and relative to the TEE imager head 3130), the sleeve can radially expand about the TEE imager head 3130 in response to the longitudinal proximal force applied by the retrieval tension member 3260. As the sleeve radially expands, the longitudinal proximal forces to overcome the friction fit decrease.

In some instances, the sleeve of the coupling member 3250 can allow for a softer and thinner material to be used, thereby reducing potential complications due to contact with, for example, the esophagus of the patient. For example, with the sleeve configured to circumscribe and slide about and/or along the TEE device 3100, the sleeve can be formed of soft and relatively thin material.

Figure 16:
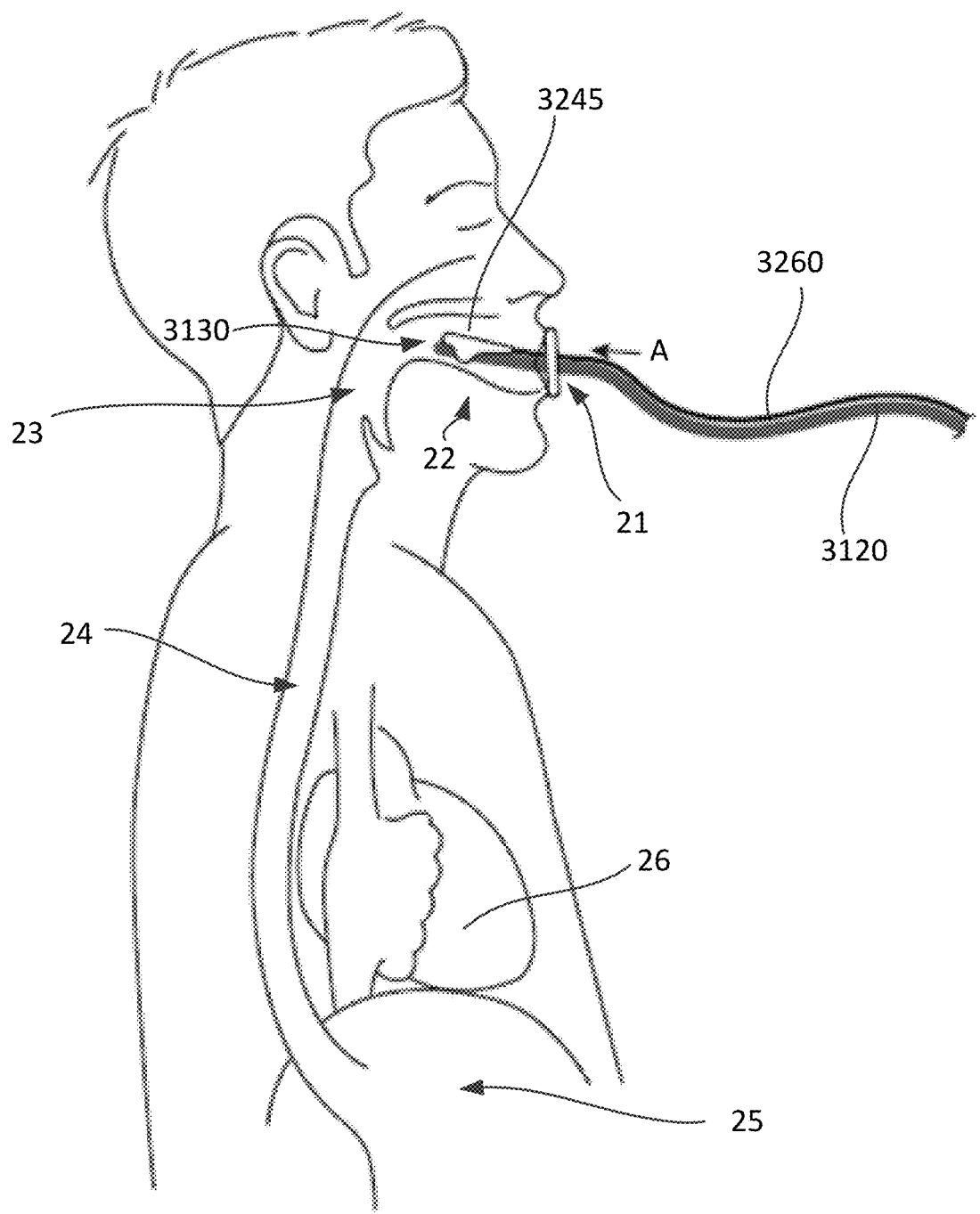
FIGS. 16-19 are schematic illustrations of the CAD of FIG. 14 in various stages of assisting a TEE intubation.
Figure 17:
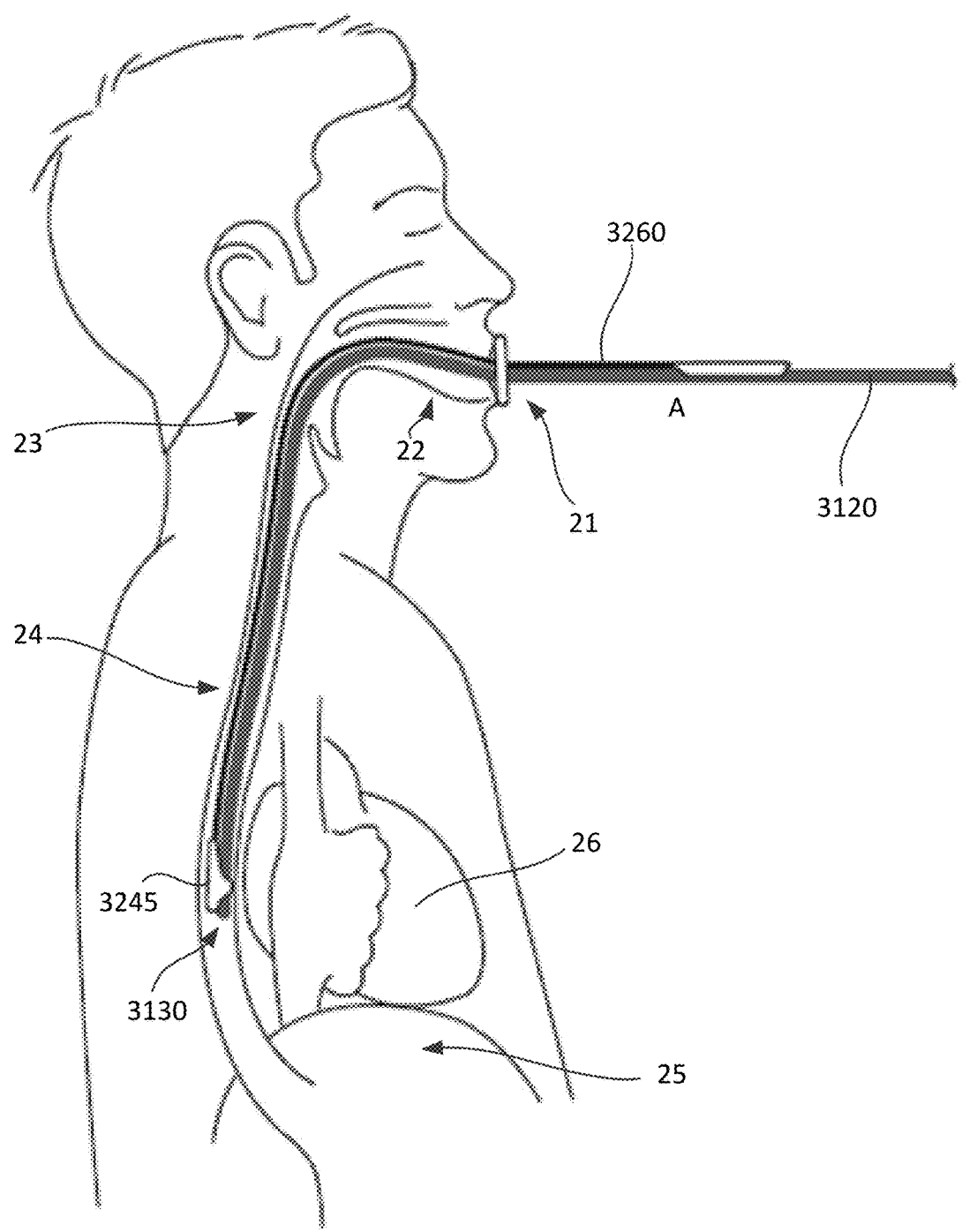

In use, to assist intubation of the TEE probe 3100, the image capture assembly 3245 of the CAD 3200 is removably attached to the TEE imager head 3130 of the TEE device 3100, and inserted with the TEE imager head 3130 into the mouth 21 of the patient, as shown in FIG. 16. As described with respect to previous embodiments, the image capture device 3240 of the image capture assembly 3245 is configured to capture and send image data in real-time (i.e., during the intubation procedure) to the graphical display device 3210 disposed outside the patient. With access to a graphical illustration of such image data, and with the image capture assembly 3245 inserted through the mouth 22, the operator can move (in the direction illustrated by arrow A) the TEE imager head 3130 and the image capture assembly 3245 toward and through the oral cavity 22 of the patient. Further, while viewing a real-time graphical representation of the patient's anatomy surrounding and/or downstream of the image capture assembly 3250 and the TEE imager head 3230, the operator can move the TEE imager head 3130 distally towards and into the esophagus 24 of the patient until the TEE imager head 3130 reaches a target region (as evidenced by the graphical representation of the image data captured by the image capture device 3240), as shown in FIG. 17.

Figure 18:
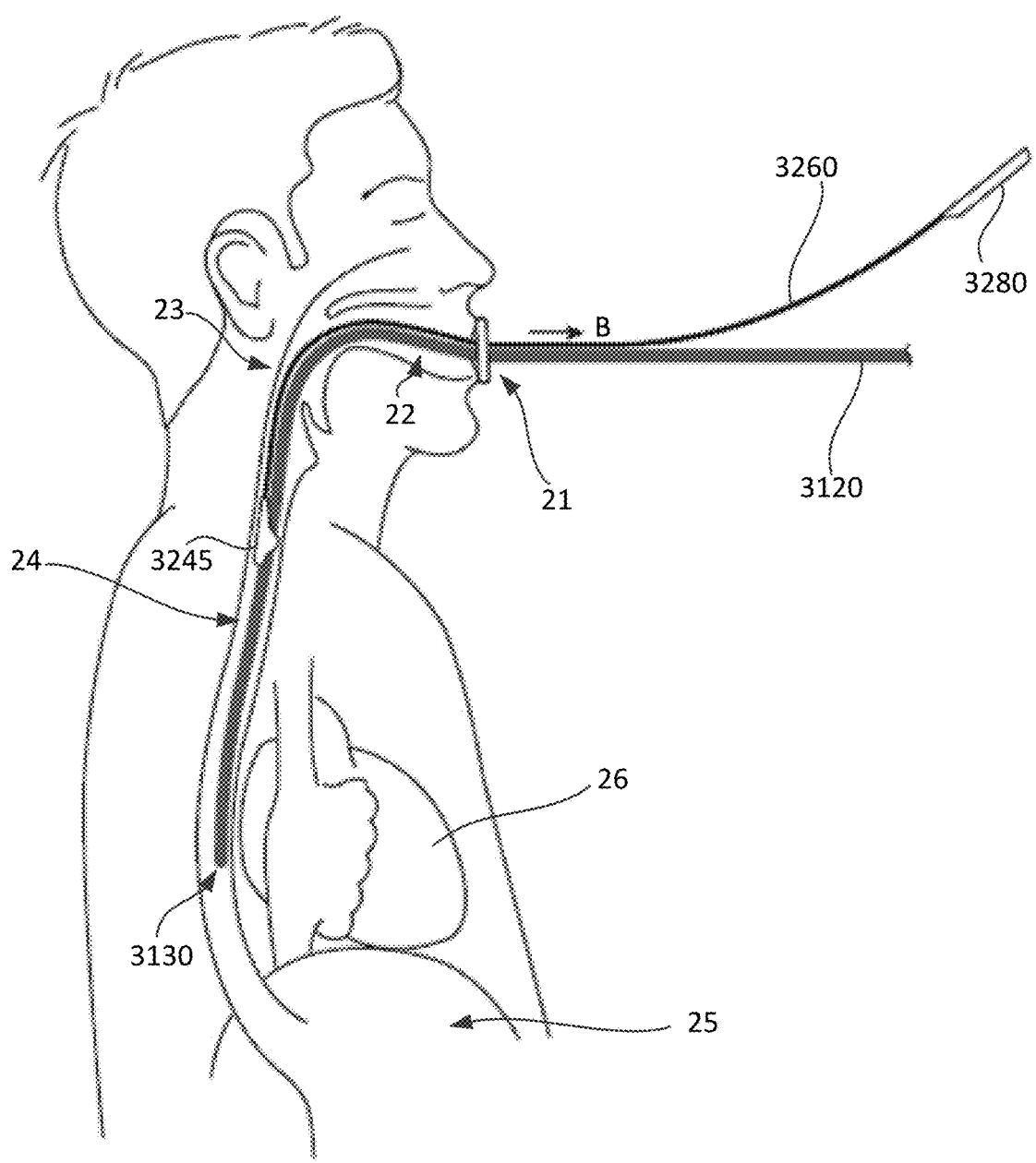
Figure 19:
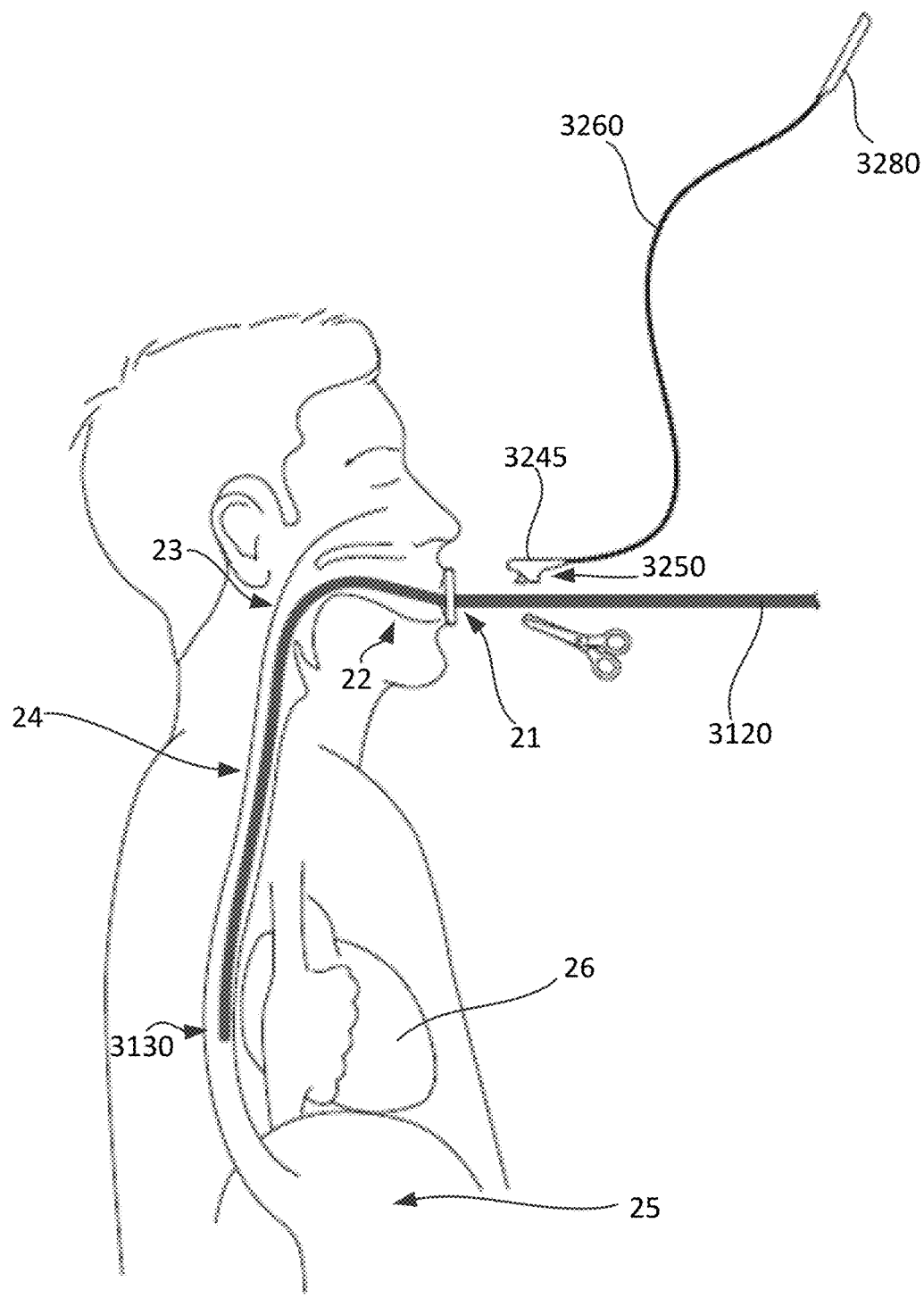

With the TEE imager head 3130 located within the target region of the esophagus, the operator can decouple the CAD handle 3280 from the TEE body 3220, and pull the CAD handle 3280 proximally to slidably release the coupling member 3250 from the TEE device 3100, as described in further detail above. As shown in FIG. 18, with the coupling member 3250 slidably released from the TEE device 3100, the operator can further pull the CAD handle 3280 proximally (in the direction illustrated by arrow B) such that the retrieval tension member 3260 and the image capture assembly 3245 are withdrawn proximally through the esophagus 24 of the patient, leaving the TEE imager head 3130 disposed within the target region of the esophagus 24, as shown in FIG. 18. More specifically, as shown, the operator can pull the CAD handle 3280 proximally such that the image capture assembly 3245 slides proximally about and along the TEE body 3120 of the TEE device 3100 through the esophagus 24 of the patient. As shown in FIG. 19, the operator can further pull the CAD handle 3280 proximally to slide the image capture assembly 3245 along the TEE body 3120 and out the mouth 21 of the patient. Further as shown in FIG. 19, with the image capture assembly 3250 removed from the patient, the coupling member 3250 can be detached completely (e.g., cut) from the TEE body 3120 (and in turn the TEE device 3100).

Figure 20:
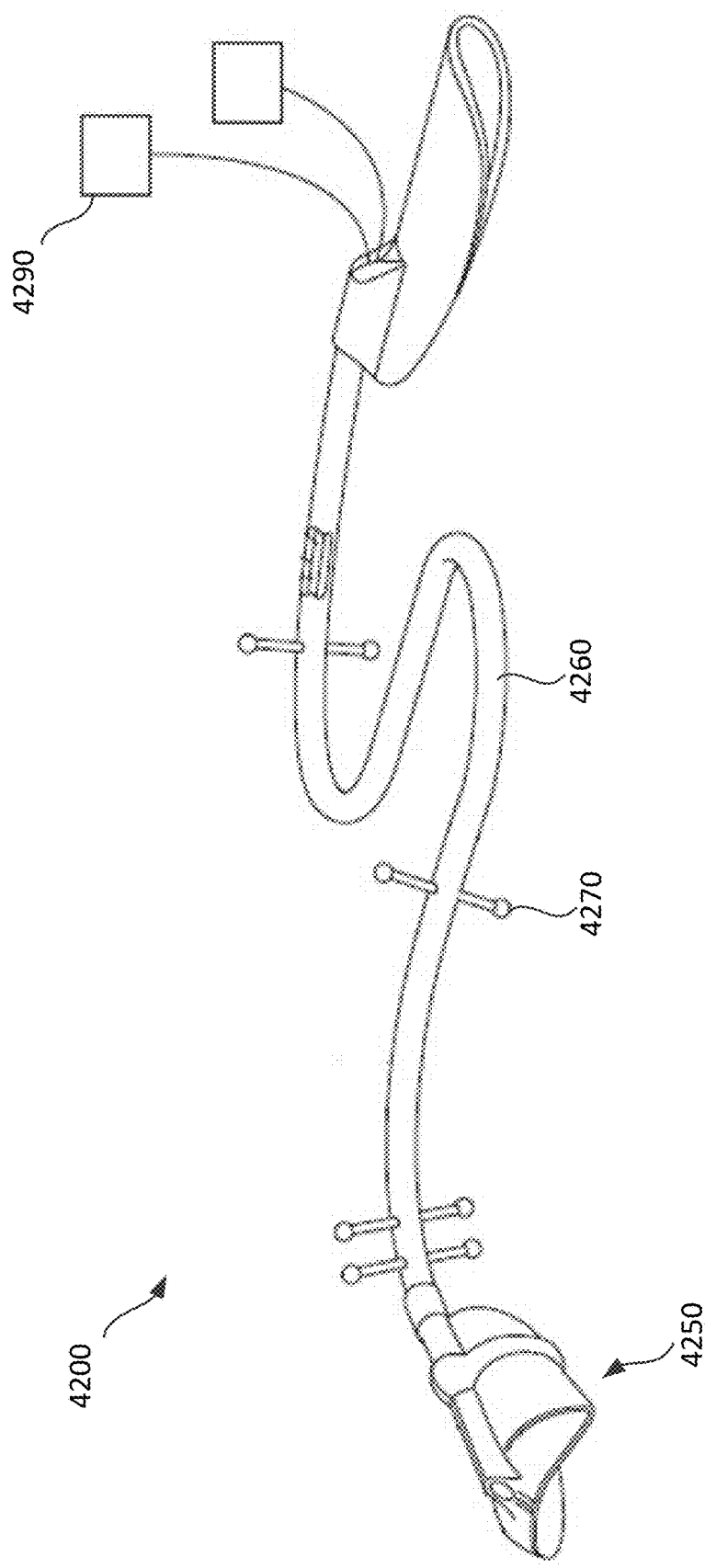
FIG. 20 is a perspective view of an image capture assembly of a CAD releasably attached to a portion of a TEE device, according to an embodiment.

FIG. 20 illustrates an embodiment of a CAD 4200 that can be used to assist intubation of a TEE probe (also referred to herein as "TEE device"). The CAD 4200 can be constructed and function similar to any of the CADs described herein, e.g., the CAD 1200, the CAD 2200, the CAD 3200, etc.). Thus, some details regarding the CAD 4200 are not described below. It should be understood that for features and functions not specifically discussed, those features and functions can be the same as or similar to any of the CADs described herein.

As described with respect to previous embodiments, during retrieval and removal of a CAD from the digestive system of the patient, it is desirable to limit and/or prevent excessive contact with the esophagus (e.g., trauma to the wall of the esophagus, esophageal and/or pharyngeal perforation) and associated anatomy by the CAD. Said another way, with the coupling member decoupled from the TEE imager head, it is desirable to control and/or define at least in part a removal profile of the CAD from patient. To that end, in this embodiment, the CAD 4200 includes multiple tension couplers 4270, configured to slidably engage with the TEE body (not shown) of the TEE device (not shown). With the tension coupler 4270 slidably coupled to and/or engaged with the TEE body, and with the TEE device and the CAD 4200 disposed in the esophagus and the coupling member 4250 of the CAD 4200 released from the TEE imager head, the retrieval tension member 4260 can be controlled and/or retained close to the TEE body as the retrieval tension member 4260 is withdrawn proximally through the esophagus and out the mouth of the patient. In this manner, the CAD 4200 can be withdrawn through the esophagus in a controlled manner to limit and/or avoid undesirable contact with surrounding anatomy. Said another way, the tension coupler 4270 can define at least in part a removal profile of the CAD 4200 through the digestive system of the patient.

In this embodiment, each of the tension couplers 4270 includes a magnetic mechanism configured to releasably attach to the TEE body by magnetic force, or to couple the opposite ends of each tension coupler 4270 to each other. In some instances, the magnetic mechanism can include permanent magnets, while in other instances, the magnetic mechanism can include an electromagnetic mechanism. In some instances, the tension couplers 4270 can include a combination of permanent magnets and electromagnetic mechanisms. In either case, for example, as an operator pulls or otherwise manipulates the CAD handle 4280 and/or the retrieval tension member 4260 to withdraw the CAD 4200 from the patient, a distance between the retrieval tension member 4260 and the TEE body is defined and/or limited by the length of each tension coupler 427, with the ends held together by one or both of the permanent magnet or the electromagnetic mechanism when energized. In instances in which the tension coupler 4270 includes an electromagnetic mechanism, the electromagnetic mechanism can be controlled (i.e., energized and/or deenergized) from the CAD controller 4290 to release the tension coupler 4270 (and in turn at least a portion of the retrieval tension member 4260) from the TEE body.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components and/or features of the different embodiments described.

The invention claimed is:

1. A method for assisting intubation of a transesophageal echocardiography (TEE) ultrasound probe device with a proximal portion and a distal portion and an ultrasound transducer disposed at the distal portion, comprising:
    inserting the distal portion of the TEE ultrasound probe device having coupled thereto via a coupling member an image capture device into an oral cavity of a patient, the coupling member being releasably attached to the distal portion of the TEE ultrasound probe device such that the coupling member contiguously and entirely circumscribes the distal portion of the TEE ultrasound probe device during the inserting;
    viewing, after the inserting, a display of image data of an esophagus of the patient captured by the image capture device;
    while viewing the display of image data, and with the image capture device attached to the distal portion of the TEE ultrasound probe device via the coupling member, passing the distal portion of the TEE ultrasound probe device through the esophagus and maneuvering the TEE ultrasound probe device to dispose the ultrasound transducer in a proper position for capturing ultrasound images of a heart;
    with both the distal portion of the TEE ultrasound probe device and the image capture device disposed within the esophagus, detaching the image capture device from the distal portion of the TEE ultrasound probe device; and
    removing, after the detaching, via the esophagus, and with the TEE ultrasound probe device disposed at least in part within the esophagus, the image capture device from the patient.

2. The method of claim 1, further comprising:
    illuminating the esophagus with an illumination device coupled to the distal portion of the TEE ultrasound probe device via the coupling member when the TEE ultrasound probe device coupled to the image capture device is disposed within the esophagus.

3. The method of claim 1, wherein the image capture device is coupled to a retrieval tension member extending from the image capture device through the esophagus and out the oral cavity of the patient when the image capture device is disposed within the esophagus,
    the removing the image capture device including applying tension to the retrieval tension member to remove the image capture device from the patient via the esophagus of the patient.

4. The method of claim 3, wherein the tension corresponds to a force of about 12-18 Newtons applied to the image capture device.

5. The method of claim 3, wherein the retrieval tension member includes a tension coupler, the TEE ultrasound probe device includes a body disposed proximal to the distal portion of the TEE ultrasound probe device, the removing the image capture device includes pulling a portion of the retrieval tension member proximally with the tension coupler slidably disposed about the body of the TEE ultrasound probe device to maintain the retrieval tension member and the image capture device proximate to the body of the TEE ultrasound probe device during the removing.

6. The method of claim 1, further comprising:
    processing, outside the patient, the image data captured by the image capture device to produce the display of image data, the display of image data being a graphical representation of the image data.

7. The method of claim 1, wherein the image capture device is coupled to a retrieval tension member extending from the image capture device through the esophagus and out a mouth of the patient when the image capture device is disposed within the esophagus, the method further comprising:
    outside the patient, releasably attaching a handle to a proximal portion of the TEE ultrasound probe device, the handle being coupled to the retrieval tension member.

8. The method of claim 1, wherein
    the TEE ultrasound probe device includes an imaging array, the method further comprising:
    viewing a display of image data of a heart of the patient captured by the imaging array, the image data of the heart captured by the imaging array being based on sound waves received at the imaging array through a portion of the coupling member, the portion of the coupling member being substantially transparent to the sound waves.

9. The method of claim 1, wherein the image capture device is coupled to a retrieval tension member extending from the image capture device through the esophagus and out the oral cavity of the patient when the image capture device is disposed within the esophagus,
    the detaching the image capture device from the distal portion of the TEE ultrasound probe device including applying tension to the retrieval tension member,
    the removing the image capture device including applying tension to the retrieval tension member to remove the image capture device from the patient via the esophagus of the patient.

10. The method of claim 9, wherein the detaching the image capture device from the distal portion of the TEE ultrasound probe device includes applying tension to the retrieval tension member such that a seam defined by the image capture assembly is at least partially opened in response to the applied tension.

11. A method for assisting intubation of a transesophageal echocardiography (TEE) ultrasound probe device, comprising:
- inserting a distal portion of the TEE ultrasound probe device having coupled thereto via a coupling member an image capture device into an oral cavity of a patient, a body of the TEE ultrasound probe device extending proximally from the distal portion of the TEE ultrasound probe device, the coupling member being releasably attached to the distal portion of the TEE ultrasound probe device such that the coupling member contiguously and entirely circumscribes the distal portion of the TEE ultrasound probe device during the inserting;
- viewing, after the inserting, a display of image data of an esophagus of the patient captured by the image capture device;
- after the viewing, and with the image capture device attached to the distal portion of the TEE ultrasound probe device via the coupling member, passing the distal portion of the TEE ultrasound probe device through the esophagus and maneuvering the TEE ultrasound probe device to dispose the distal portion of the TEE ultrasound probe device in a proper position for capturing ultrasound images of a heart,
- a retrieval tension member extending from the image capture device through the esophagus and out the oral cavity of the patient when the image capture device is disposed within the esophagus;
- with both the TEE ultrasound probe device and the image capture device disposed within the esophagus, applying tension to the retrieval tension member to move the image capture assembly and the coupling member proximally from the distal portion of the TEE ultrasound probe device; and
- removing, via the esophagus, and with the TEE ultrasound probe device disposed at least in part within the esophagus, the image capture device from the patient.

12. The method of claim 11, wherein one or more tension couplers are engaged with both the retrieval tension member and the body of the TEE ultrasound probe device during the applying the tension such that a distance between the retrieval tension member and the body of the TEE ultrasound probe device is limited, the one or more tension couplers includes at least one of a ring, a strap, or a magnet.

13. The method of claim 11, wherein the tension corresponds to a force of about 12-18 Newtons applied to the image capture device.

14. The method of claim 11, wherein the applying tension to the retrieval tension member to move the image capture device proximally from the distal portion of the TEE ultrasound probe device includes opening a seam of the coupling member to allow longitudinal relative movement between the distal portion of the TEE ultrasound probe device and the image capture device.

15. The method of claim 11, wherein the applying tension to the retrieval tension member causes a portion of the coupling member to radially expand to reduce a force necessary to move the image capture device proximally from the distal portion of the TEE ultrasound probe device.

16. The method of claim 11, further comprising:
- illuminating the esophagus with an illumination device coupled to the TEE ultrasound probe device via the coupling member when the TEE ultrasound probe device is disposed within the esophagus.

17. The method of claim 11, wherein the retrieval tension member defines a lumen therethrough, and a communication line extends from the image capture device through the lumen of the retrieval tension member to outside the patient when both the image capture device and the TEE ultrasound probe device are disposed within the esophagus of the patient.

18. A method for assisting intubation of a transesophageal echocardiography (TEE) ultrasound probe device, comprising:
- inserting a distal portion of a TEE ultrasound probe device having coupled thereto via a coupling member an image capture device into an oral cavity of a patient, the image capture device configured to capture image data of an esophagus of the patient when disposed therein, the coupling member contiguously and entirely circumscribing the distal portion of the TEE ultrasound probe device to limit relative movement between the distal portion of the TEE ultrasound probe device and the image capture device during the inserting;
- moving the TEE ultrasound probe device coupled to the image capture device distally within the esophagus;
- with both the TEE ultrasound probe device and the image capture device disposed within the esophagus, sliding the image capture device proximally along a body of the TEE ultrasound probe device and away from the distal portion of the TEE ultrasound probe device, the coupling member contiguously and entirely circumscribing the body of the TEE ultrasound probe device during the sliding; and
- removing, after the sliding, via the esophagus, and with the TEE ultrasound probe device disposed at least in part within the esophagus, the image capture device from the patient.

19. The method of claim 18, wherein during the inserting the coupling member resists longitudinal relative movement between the distal portion of the TEE ultrasound probe device and the image capture device in response to forces below a threshold force.

20. The method of claim 19, wherein the image capture device is coupled to a retrieval tension member extending from the image capture device through the esophagus and out the oral cavity of the patient when the image capture device is disposed within the esophagus,
- the sliding the image capture device including applying tension to the retrieval tension member to apply a force exceeding the threshold force to the coupling member.

21. The method of claim 20, wherein the threshold force is about 10-15 Newtons.

22. The method of claim 20, wherein the threshold force is less than about 10 Newtons.

23. The method of claim 20, wherein the tension corresponds to a force of about 12-18 Newtons applied to the coupling member.

24. The method of claim 20, wherein the coupling member is formed of a flexible material, the coupling member radially expanding in response to the force exceeding the threshold force.

25. The method of claim 18, wherein the coupling member includes a seam, the method further comprising, with both the TEE ultrasound probe device and the image capture device disposed within the esophagus, opening the seam to allow longitudinal relative movement between the distal portion of the ultrasound probe TEE ultrasound probe device and the image capture device.

26. The method of claim 1, wherein the image capture device is coupled to a retrieval tension member extending from the image capture device through the esophagus and out the oral cavity of the patient when the image capture device is disposed within the esophagus, the removing the image capture device including applying tension proximally to the retrieval tension member to remove the image capture device from the patient via the esophagus of the patient, the retrieval tension member configured such that applying a compressive force distally to the retrieval tension member from outside the patient fails to transfer the compressive force to the image capture device disposed within the esophagus.

* * * * *